US009107831B2

(12) United States Patent
O'Hagan

(10) Patent No.: US 9,107,831 B2
(45) Date of Patent: Aug. 18, 2015

(54) IMMUNOGENIC COMPOSITIONS CONTAINING MICROPARTICLES COMPRISING ADSORBED TOXOID AND POLYSACCHARIDE-CONTAINING ANTIGENS

(75) Inventor: Derek O'Hagan, Berkeley, CA (US)

(73) Assignee: Novartis Vaccines and Diagonstics, Inc., Cambridge, MA (US)

( * ) Notice: Subject to any disclaimer, the term of this patent is extended or adjusted under 35 U.S.C. 154(b) by 0 days.

(21) Appl. No.: 10/858,858

(22) Filed: Jun. 2, 2004

(65) Prior Publication Data

US 2005/0118275 A1   Jun. 2, 2005

Related U.S. Application Data

(60) Provisional application No. 60/475,010, filed on Jun. 2, 2003, provisional application No. 60/513,074, filed on Oct. 21, 2003.

(51) Int. Cl.

| | | |
|---|---|---|
| A61K 39/05 | (2006.01) | |
| A61K 9/50 | (2006.01) | |
| A61K 39/08 | (2006.01) | |
| A61K 47/00 | (2006.01) | |
| A61K 45/00 | (2006.01) | |
| A61K 39/02 | (2006.01) | |
| A61B 5/055 | (2006.01) | |
| A61K 8/30 | (2006.01) | |
| A61K 9/16 | (2006.01) | |
| A61K 39/12 | (2006.01) | |
| A61K 39/095 | (2006.01) | |
| A61K 35/74 | (2015.01) | |
| A61K 38/48 | (2006.01) | |
| A61K 39/00 | (2006.01) | |

(52) U.S. Cl.
CPC .............. *A61K 9/1647* (2013.01); *A61K 9/1641* (2013.01); *A61K 39/05* (2013.01); *A61K 39/08* (2013.01); *A61K 39/095* (2013.01); *A61K 39/12* (2013.01); *A61K 9/1652* (2013.01); *A61K 35/74* (2013.01); *A61K 38/4893* (2013.01); *A61K 2039/55505* (2013.01); *A61K 2039/55555* (2013.01); *A61K 2039/6037* (2013.01); *A61K 2039/6087* (2013.01); *A61K 2039/6093* (2013.01); *C12N 2730/10134* (2013.01); *C12N 2770/32434* (2013.01); *C12N 2770/32634* (2013.01)

(58) Field of Classification Search
CPC ..... A61K 9/1652; A61K 39/05; A61K 39/08; A61K 35/74; A61K 38/4893
USPC .............................................. 424/489, 278.1
See application file for complete search history.

(56) References Cited

U.S. PATENT DOCUMENTS

| | | | |
|---|---|---|---|
| 5,783,567 A | 7/1998 | Hedley et al. | |
| 5,869,103 A | 2/1999 | Yeh et al. | |
| 5,871,747 A | 2/1999 | Gengoux-Sedlik et al. | |
| 5,902,565 A * | 5/1999 | Cox et al. | 424/1.29 |
| 5,981,719 A | 11/1999 | Woiszwillo et al. | 530/410 |
| 6,001,395 A * | 12/1999 | Coombes et al. | 424/501 |

(Continued)

FOREIGN PATENT DOCUMENTS

| | | | |
|---|---|---|---|
| WO | WO 94/15635 | 7/1994 | ........... A61K 39/385 |
| WO | WO 94/28879 | 12/1994 | |

(Continued)

OTHER PUBLICATIONS

Singh et al (Immunogenicity and protection in small-animal models wit controlled-release tetanus toxoid microparticles as a single dose vaccine, Infection and Immunity, 1997; 65(5): 1716-21).*

(Continued)

*Primary Examiner* — Gary Nickol
*Assistant Examiner* — Lakia Tongue
(74) *Attorney, Agent, or Firm* — Helen Lee

(57) ABSTRACT

Immunogenic compositions comprising microparticles with adsorbed toxoid antigen and/or polysaccharide-containing antigen are disclosed. The immunogenic microparticle compositions comprise (a) polymer microparticles comprising a biodegradable polymer; (b) an antigen adsorbed to the microparticles selected from (i) a toxoid antigen, such as a tetanus toxoid, a diphtheria toxoid, or a combination thereof, and/or (ii) a polysaccharide containing antigen, such as a Hib polysaccharide antigen, a Hib conjugate antigen comprising polysaccharide and polypeptide regions, a meningococcal polysaccharide antigen, a meningococcal conjugate antigen comprising polysaccharide and polypeptide regions, a pneumococcal polysaccharide antigen, and a pneumococcal conjugate antigen comprising polysaccharide and polypeptide regions or a combination thereof; and (c) a pharmaceutically acceptable excipient. The biodegradable polymer can be, for example, a polymer selected from a poly(α-hydroxy acid), a polyhydroxy butyric acid, a polycaprolactone, a polyorthoester, a polyanhydride, and a polycyanoacrylate. Also disclosed are methods of immunization against infection by a pathogenic organisms and methods stimulating immune responses, which comprise administering such compositions to host animals. Methods of producing such microparticle compositions are also disclosed which comprise forming a water-in-oil-in-water emulsion that contains water, organic solvent and biodegradable polymer, followed by removal of the organic solvent from the emulsion to form microparticles, after which toxoid and/or polysaccharide containing antigens are adsorbed on the microparticles.

44 Claims, 3 Drawing Sheets

(56) References Cited

U.S. PATENT DOCUMENTS

| | | | |
|---|---|---|---|
| 6,007,845 A | 12/1999 | Domb et al. | 424/501 |
| 6,086,901 A | 7/2000 | O'Hagan et al. | 424/283.1 |
| 6,207,171 B1* | 3/2001 | Payne et al. | 424/280.1 |
| 6,309,669 B1* | 10/2001 | Setterstrom et al. | 424/486 |
| 6,884,435 B1* | 4/2005 | O'Hagan et al. | 424/489 |
| 2002/0002272 A1 | 1/2002 | Houghton et al. | 530/388.3 |
| 2002/0025329 A1 | 2/2002 | O'Hagan et al. | 424/278.1 |
| 2002/0136776 A1* | 9/2002 | Fang et al. | 424/501 |
| 2002/0155436 A1 | 10/2002 | Classen | 435/5 |
| 2003/0021766 A1 | 1/2003 | Vajdy et al. | 424/93.2 |
| 2003/0049298 A1 | 3/2003 | O'Hagan et al. | 424/418 |
| 2003/0082213 A1 | 5/2003 | O'Hagan et al. | 424/278.1 |
| 2003/0138453 A1 | 7/2003 | O'Hagan et al. | 424/199.1 |
| 2003/0138458 A1 | 7/2003 | Houghton et al. | 424/225.1 |
| 2003/0170273 A1 | 9/2003 | O'Hagan et al. | 424/225.1 |
| 2004/0022814 A1 | 2/2004 | O'Hagan et al. | 424/277.1 |
| 2004/0101537 A1 | 5/2004 | O'Hagan et al. | 424/249.1 |
| 2004/0258703 A1* | 12/2004 | Glenn et al. | 424/184.1 |
| 2005/0107322 A1* | 5/2005 | O'Hagan et al. | 514/44 |
| 2006/0002949 A1* | 1/2006 | Glenn et al. | 424/185.1 |

FOREIGN PATENT DOCUMENTS

| | | | |
|---|---|---|---|
| WO | WO 96/20698 | 7/1996 | |
| WO | 97/02810 A2 | 1/1997 | |
| WO | WO 97/02810 | 1/1997 | A61K 9/16 |
| WO | WO 97/24447 | 7/1997 | C12N 15/63 |
| WO | WO 98/10750 | 3/1998 | A61K 9/16 |
| WO | 98/33487 A1 | 8/1998 | |
| WO | 00/06123 A1 | 2/2000 | |
| WO | WO 00/50006 | 8/2000 | A61K 9/107 |
| WO | 00/56362 A2 | 9/2000 | |
| WO | WO 01/36599 A1 | 5/2001 | C12N 5/06 |
| WO | 01/81609 A2 | 11/2001 | |
| WO | 02/26209 A2 | 4/2002 | |
| WO | WO 02/26212 A2 | 4/2002 | A61K 9/16 |
| WO | WO 03/002065 A2 | 1/2003 | |
| WO | 03/028656 A2 | 4/2003 | |
| WO | WO 03/028661 A2 | 4/2003 | |
| WO | 03/070909 A2 | 8/2003 | |

OTHER PUBLICATIONS

Fahey et al (Status of immune-based therapies in HIV infection and AIDS, Clin. Exp. Immunol., 1992, 88, 1-5).*
Boslego, J. et al (Gonorrhea Vaccines , Chapter 17, 211-223).*
Ellis, R (New Technologies for Making Vaccines, text book, 1998, 568-575).*
adsorb definition: http://www.mercksource.com/pp/us/cns/cns_hl_dorlands_split.jsp?pg=/ppdocs/us/common/dorlands/dorland/one/000001949.htm, accessed May 26, 2009).*
Yang et al. (Journal of Pharmaceutical Sciences, 1997; 86(8): 908-914).*
Chen et al. (Nucleic Acids Research, 2002; 30(6): 1338-1345).*
M. Briones et al., "The Preparation, Characterization, and Evaluation of Cationic Microparticles for DNA Vaccine Therapy," *Pharmaceutical Research*, vol. 18, No. 5, 2001, pp. 709-712.
J. Kazzaz et al., "Novel Anionic Microparticles Are a Potent Adjuvant for the Induction of Cytotoxic T Lymphocytes Against Recombinant p55 Gag from HIV-1," *Journal of Controlled Release*, vol. 67, 2000, pp. 347-356.
K.S. Denis-Mize et al., "Plasmid DNA Adsorbed onto Cationic Microparticles Mediates Target Gene Expression and Antigen Presentation by Dendritic Cells," *GeneTherapy*, vol. 7, 2000, pp. 2105-2112.
Manmohan Singh et al., "Cationic Microparticles Are an Effective Delivery System for Immune Stimulatory CpG DNA," *Pharmaceutical Research*, vol. 18, No. 10, Oct. 2001, pp. 1476-1479.
Manmohan Singh et al., "Cationic Microparticles: A Potent Delivery System for DNA Vaccines," *Proceedings of the National Academy of Science USA*, vol. 97, No. 2, Jan. 18, 2000, pp. 811-816.
Manmohan Singh et al., "Mucosal Immunization with HIV-1 Gag DNA on Cationic Microparticles Prolongs Gene Expression and Enhances Local and Systemic Immunity," *Vaccine*, vol. 20, 2002, pp. 594-602.
Derek O'Hagan et al., "Induction of Potent Immune Responses by Cationic Microparticles with Adsorbed Human Immunodeficiency Virus DNA Vaccines," *Journal of Virology*, vol. 75, No. 19, Oct. 2001, pp. 9037-9043.
CDC Morbidity and Mortality Weekly Report. Recommendations and Reports. Combination Vaccines for Childhood Immunization, vol. 48, No. RR-S. May 14, 1999. http://www.cdc.gov/mmwr/PDF/rr/rr4805.pdf.
Canada Division of Immunization & Respiratory Diseases. Vaccine Preventable Diseases. http://www.hc-sc.gc.ca/pphb-dgspsp/dird-dimr/vpd-mev/index.html. Oct. 5, 2004 download, 117 pages total.
The Expanded Programme on Immunization. Fact Sheet. http://dcc2.bumc.bu.edu/IH887/immpap97.htm. Oct. 5, 2004 download, pp. 1-9.
Recommended Childhood and Adolescent Immunization Schedule—United States, 2003. http://www.or.regence.com/provider/clinicalCorner/docs/childSchedule2003.pdf, 2 pages.
Manmohan Singh et al., "Immunogenicity and Protection in Small-Animal Models with Controlled-Release Tetanus Toxoid Microparticles as a Single-Dose Vaccine," *Infection and Immunity*, vol. 65, No. 5, May 1997, pp. 1716-1721.
Derek T. O'Hagan et al., "Microparticles as Vaccine Adjuvants and Delivery Systems," *Expert Rev. Vaccines*, vol. 2, No. 2, 2003, pp. 269-283.
Manmohan Singh et al., "Controlled Release Microparticles as a Single Dose Diphtheria Toxoid Vaccines: Immunogenicity in Small Animal Models," *Vaccine*, vol. 16, No. 4, 1998, pp. 346-352.
M. Peyre, D. Sesardic, H.P. Merkle, B. Gander and P. Johansen, "Divalent Microsphere Vaccines are Protective Against Tetanus and Diphtheria", *Proceed. Int'l Symp. Control. Rel. Bioact. Mater.*, 28 (2001), Controlled Release Society , Inc., p. 1077-1078.
Almeida, Antonio J. et al., "Poly(lactic acid) microspheres as immunological adjuvants for orally delivered cholera toxin B subunit," *Biochemcial Society Transactions* (1992) 20, p. 316S.
Almeida, Antonio J., et al., "Immune Response to Nasal Delivery of Antigenically Intact Tetanus Toxoid Associated with Poly(L-lactic acid) Microspheres in Rats, Rabbits and Guinea-pigs," *J. Pharm. Pharmacol.* 1993, 45: 198-203, pp. 198-203.
Jackson, Raymond J., "Oral Vaccine Models: Multiple Delivery Systems Employing Tetanus Toxoid," *Annals New York Academy of Sciences*, 1994, vol. 730, pp. 217-234.
Duncan, Jacqueline D. et al., "Poly(lactide-co-glycolide) Microencapsulation of Vaccines for Mucosal Immunization," *Mucosal Vaccines*, 1996, pp. 159-173.
Alpar, H.O., et al., Immune Responses to Mucosally Administered Tetanus Toxoid in Biodegradable Microspheres, *Proceed. Intern. Symp. Control. Rel. Bioact. Mater.*, 21 (1994), pp. 867-868.
O'Hagan, Derek et al., "Long-Term Antibody Responses in Mice Following Subcutaneous Immunization With Ovalbumin Entrapped in Biodegradable Microparticles," Vaccine, vol. 11, 1993, pp. 1965-1969.
Coombes, A.G.A. et al., "Single Dose, Polymeric, Microparticle-Based Vaccines: The Influence of Formulation Conditions on the Magnitude and Duration of the Immune Response to a Protein Antigen," Vaccine, vol. 14, No. 15, 1996, pp. 1429-1438.
Eldridge, J. et al., "Biodegradable and Biocompatible Poly(DL-Lactide-Co-Glycolide) Microspheres As an Adjuvant for Staphylococcal Enterotoxin B Toxoid Which Enhances the Level of Toxin-Neutralizing Antibodies," Infection and Immunity, vol. 59, No. 9, Sep. 1991, pp. 2978-2986.
Eldridge, J. et al., "New Advances in Vaccine Delivery Systems," Seminars in Hemotology, vol. 30, No. 4, Suppl. 4, Oct. 1993, pp. 16-25.
Higgins, D. et al., "MF59 Adjuvant Enhances the Immunogenicity of Influenza Vaccine in Both Young and Old Mice," Vaccine, vol. 14, No. 6, 1996, pp. 478-484.
Men, Y. et al., "Induction of a Cytotoxic T Lymphocite Response by Immunization With a Malaria Specific CTL Peptide Entrapped in Biodegradable Polymer Microspheres, "Vaccine, vol. 15, No. 12/13, 1997, pp. 1405-1412.

(56) References Cited

OTHER PUBLICATIONS

Moore, A. et al., "Immunization With a Soluble Recombinant HIV Protein Entrapped in Biodegradable Microparticles Induces HIV-Specific CD8+ Cytotoxic T Lymphocites and CD4+ TH1 Cells," Vaccine, vol. 13, No. 18, 1995, pp. 1741-1995.

Nakaoka, R. et al., "Enhanced Antibody Production Through Sustained Antigen Release From Biodegradable Granules," Journal of Controlled Release, vol. 37 (1995), pp. 215-224.

O'Hagan, Derek et al., Biodegradable Microparticles for Oral Immunization, Vaccine, vol. 11, 1993, pp. 149-154.

Sah, H. et al., "Continuous Release of Proteins From Biodegradable Microcapsules and in Vivo Evaluation of Their Potential As a Vaccine Adjuvant," Journal of Controlled Release 35 (1995), pp. 137-144.

Vordermeier, H.M. et al., "Synthetic Delivery System for Tuberculosis Vaccines: Immunological Evaluation of the *M. tuberculosis* 38 kDa Protein Entrapped in Biodegradable PLG Microparticles," Vaccine, vol. 13, No. 16, 1995, pp. 1576-1582.

Fattal, Elias et al., "Biodegradable polyalklcyanoacrylate nanpparticles for the delivery of olionucleotides," Journal of Controlled Release 53 (1998), pp. 137-143.

Chavany, Christine et al., "Adsorption of Oligonucleotides onto Polyisohexylcyanoacrylate Nanoparticles Protects Them Against Nucleases and Increases Their Cellular Uptake," Pharmaceutical Research, vol. 11, No. 9, 1994, pp. 1370-1378.

A. Spickler et al., "Adjuvants in Veterinary Vaccines: Modes of Action and Adverse Effects", J Vet Intern Med 2003;17:273-281.

J. Cox et al., "Adjuvants—A Classification and Review of Their Modes of Action", Vaccine, vol. 15, No. 3, pp. 248-256, 1997.

N. Burdin et al., "Immunological Foundations to the Quest for New Vaccine Adjuvants", Biodrugs 2004; 18 (2): 79-93.

Notice of Opposition, dated Apr. 29, 2010, filed in the counterpart European Patent EP1631264B1.

Boehm, G. et al. "On technological and immunological benefits of multivalent single-injection microsphere vaccines," Pharmaceutical Research, vol. 19, No. 9, 2002, pp. 1330-1336.

Hall, A. et al. "Practice in Developing Countries," The Lancet, vol. 335, 1990, pp. 774-777.

Somavarapu, S. et al. "The Immune Responses Following Nasal and Intra Muscular Administration of Tetanus Toxoid Adsorbed on PLA Lamellae," Journal of Pharmacy and Pharmacology, vol. 51 (Supplement), 1999, p. 124.

Van De Weert, M. et al. "Protein Instability in Poly(Lactic-co-Glycolic Acid)," Pharmaceutical Research, vol. 17, No. 10, 2000, pp. 1159-1167.

Peyre, M. et al. "An experimental divalent vaccine based on biodegradable microspheres induces protective immunity against tetanus and diphtheria," Journal of Pharmaceutical Sciences, vol. 92, No. 5, 2003, pp. 957-966.

Jabbal-Gill, I. et al. "Potential of polymeric lamellar substrate particles (PLSP) as adjuvants for vaccines," Vaccine, vol. 18, 2000, pp. 238-250.

Jung, T. et al. "Tetanus toxoid loaded nanoparticles from sulfobutylated poly(vinyl alcohol)-graft-poly(lactide-co-glycolide): Evaluation of antibody response after oral and nasal application in mice," Pharmaceutical Research, vol. 18, No. 3, 2001, pp. 352-360.

Marks, M. et al. "Immunization today—a review," C.M.A Journal, vol. 108, 1973, pp. 1413-1418.

Hinman, A. et al. "Immunisation Practice in Developed Countries," The Lancet, vol. 335, pp. 707-710.

\* cited by examiner

IMMUNOGENIC COMPOSITIONS CONTAINING MICROPARTICLES COMPRISING ADSORBED TOXOID AND POLYSACCHARIDE-CONTAINING ANTIGENS

STATEMENT OF RELATED APPLICATIONS

This application claims the benefit of U.S. provisional patent application No. 60/475,010 filed Jun. 2, 2003, which is incorporated herein by reference in its entirety. This application also claims the benefit of U.S. provisional patent application No. 60/513,074 filed Oct. 21, 2003, which is incorporated herein by reference in its entirety.

FIELD OF THE INVENTION

The present invention relates to immunogenic pharmaceutical compositions, particularly vaccine compositions.

BACKGROUND

The emergence of subunit vaccines, including polypeptide, polysaccharide, conjugate, and DNA vaccines, has intensified the need for safe and effective adjuvant-containing compositions.

Currently, the most commonly used adjuvants in the United States are alum adjuvants (i.e., aluminum salts such as aluminum hydroxide and aluminum phosphate). Only alum is currently approved for human use by the U.S. Department of Health and Human Services, Food and Drug Administration (FDA). For example, various diphtheria-tetanus vaccines are available in which diphtheria toxoids and tetanus toxoids are adsorbed to aluminum salts. Although aluminum adjuvants have a demonstrated safety profile of many years, these adjuvants are nonetheless occasionally associated with local reactions. For example, post-vaccination granulomas are a well-known reaction associated with aluminum-adsorbed vaccines.

Particulate carriers have been used with adsorbed or entrapped antigens in attempts to elicit adequate immune responses. Such carriers typically present multiple copies of a selected recombinant protein antigen to the immune system and promote trapping and retention of antigens in local lymph nodes. The particles can be phagocytosed by macrophages and can enhance antigen presentation through cytokine release.

For example, commonly owned International patent application WO 98/33487 and co-pending U.S. patent application Ser. No. 09/015,652, filed Jan. 29, 1998, describe the use of antigen-adsorbed and antigen-encapsulated microparticles to stimulate immunological responses, including cell-mediated immunological responses, as well as methods of making the microparticles. Polymers used to form the microparticles include poly(lactide) and poly(lactide-co-glycolide), also referred to herein as "PLG".

Commonly owned International patent application WO 00/06123 and co-pending U.S. patent application Ser. No. 09/715,902 disclose methods of making microparticles having adsorbed macromolecules, including DNA, polypeptides, antigens and adjuvants. The microparticles comprise, for example, a polymer such as a poly(alpha-hydroxy acid) (e.g., PLG), a polyhydroxy butyric acid, a polycaprolactone, a polyorthoester, a polyanhydride, and the like and are formed using, for example, cationic, anionic or nonionic detergents. Microparticles containing anionic detergents, such as PLG microparticles with sodium dodecyl sulfate (SDS), are proposed for the use of positively charged macromolecules, such as polypeptides. Microparticles containing cationic detergents, such as PLG microparticles with CTAB (cetyltrimethylammonium bromide), are proposed for the use of negatively charged macromolecules, such as DNA. The use of such microparticles to stimulate immunological responses, including cell-mediated immunological responses, is also disclosed.

SUMMARY OF THE INVENTION

The present invention relates to immunogenic compositions comprising biodegradable polymer microparticles having toxoid and polysaccharide-containing antigens adsorbed thereto.

According to a first aspect of the invention, an immunogenic composition is provided which comprises: (a) polymer microparticles comprising a biodegradable polymer, for example, a polymer selected from a poly($\alpha$-hydroxy acid), a polyhydroxy butyric acid, a polycaprolactone, a polyorthoester, a polyanhydride, and a polycyanoacrylate; (b) an antigen adsorbed to the microparticles selected from (i) a toxoid antigen, such as a tetanus toxoid, a diphtheria toxoid, or a combination thereof, and/or (ii) a polysaccharide containing antigen, such as a Hib polysaccharide antigen, a Hib conjugate antigen comprising polysaccharide and polypeptide regions, a meningococcal polysaccharide antigen, a meningococcal conjugate antigen comprising polysaccharide and polypeptide regions, a pneumococcal polysaccharide antigen, a pneumococcal conjugate antigen comprising polysaccharide and polypeptide regions, or a combination thereof; and (c) a pharmaceutically acceptable excipient. Typically, microparticles are prepared via any of a variety of techniques, after which the antigen is adsorbed to the microparticles.

In many embodiments, the microparticles are formed from a poly($\alpha$-hydroxy acid), such as a poly(lactide) ("PLA"), a copolymer of lactide and glycolide, such as a poly(D,L-lactide-co-glycolide) ("PLG"), or a copolymer of D,L-lactide and caprolactone. Poly(D,L-lactide-co-glycolide) polymers include those having a lactide:glycolide molar ratio ranging, for example, from 20:80 to 80:20, from 25:75 to 75:25, from 40:60 to 60:40, or from 55:45 to 45:55, and having a molecular weight ranging, for example, from 5,000 to 200,00 Daltons, from 10,000 to 100,000 Daltons, from 20,000 to 70,000 Daltons, or from 40,000 to 50,000 Daltons.

In many embodiments, the immunogenic compositions will comprise antigens in addition to toxoid and/or polysaccharide-containing antigens. These additional antigens may independently be, for example: (a) adsorbed to the surface of the microparticles, (b) entrapped within the microparticles, (c) in solution or suspension, (d) adsorbed to separate populations of microparticles, and/or (e) entrapped within separate populations of microparticles.

Antigens can be, for example, killed or attenuated pathogens (e.g., bacteria, viruses, fungi or parasites) or cells (e.g., tumor cells), polypeptide containing antigens, polysaccharide containing antigens, toxoids, or polynucleotide containing antigens.

Examples of polynucleotide-containing antigens include, for example, (a) nucleic acid sequences that directly encode polypeptide-containing antigens (e.g., an mRNA molecule) and (b) vector constructs that indirectly encode polypeptide-containing antigens, for example, vector constructs that express heterologous nucleic acid sequences, which in turn encode polypeptide-containing antigens (e.g., DNA vector constructs and RNA vector constructs). The encoded polypeptide-containing antigens can be, for example, tumor antigens and/or antigens derived from pathogenic organisms.

Similarly, polypeptide containing antigens and polysaccharide containing antigens can be, for example, tumor antigens and/or pathogenic organism antigens. Thus, in some embodiments, these antigens are derived from tumors. In other embodiments, the antigens are derived from viruses, for example, hepatitis virus, herpes simplex, human immunodeficiency virus, varicella virus, polio, measles, mumps, rubella, cytomegalovirus and influenza virus. In other embodiments, the antigens are derived from bacteria such as, for example, diphtheria, tetanus, pertussis, *Neisseria meningitidis, Haemophilus influenza* (e.g., *Haemophilus influenza* type b), *streptococcus, Neisseria gonorrhoeae, Helicobacter pylori*, and cholera. In still other embodiments, the antigens are derived from fungi, or from parasites such as, for example, a malaria parasite.

Specific examples of antigens include various combinations of the following: (a) pertussis antigens (e.g., whole-cell and acellular pertussis antigens), (b) *Haemophilus influenzae* type b (Hib) antigens (e.g., Hib polysaccharide and Hib conjugate antigens), (c) hepatitis antigens (e.g., hepatitis A virus antigens, hepatitis C virus antigens, hepatitis D virus antigens, hepatitis E virus antigens, hepatitis G virus antigens, and combinations thereof, e.g., hepatitis A-B); (d) polio antigens (e.g., killed and live attenuated virus antigens, typically trivalent inactivated polio antigens); (e) meningococcal (*Neisseria meningitidis*) antigens, including polysaccharide and conjugate antigens (e.g., meningitis A, meningitis B, meningitis C, meningitis W, meningitis Y and combinations, such as meningitis A-C, meningitis A-B-C, meningitis A-C-W-Y and meningitis A-B-C-W-Y); (f) pneumococcal (*Streptococcus pneumoniae*) antigens (e.g., polysaccharide and conjugate antigens); (g) varicella zoster virus (chickenpox) antigens (e.g., lyophilized, live attenuated virus antigens), (h) measles virus antigens (e.g., live attenuated virus antigens), (i) mumps virus antigens (e.g., live, attenuated virus antigens), (j) rubella virus antigen (e.g., live, attenuated virus antigens).

The immunogenic compositions of the present invention can also comprise various supplementary immunological adjuvants. As with the additional antigens above, these supplementary immunological adjuvants may independently be, for example: (a) adsorbed to the surface of the microparticles, (b) entrapped within the microparticles, (c) in solution/suspension, (d) adsorbed to separate populations of microparticles, and/or (e) entrapped within separate populations of microparticles.

Examples of supplementary immunological adjuvants include (a) immunostimulating oligonucleotides such as CpG oligonucleotides, (b) double-stranded RNA, (c) *E. coli* heat-labile toxins, (d) liposaccharide phosphate compounds (e.g., monophosphorylipid A and derivatives) and liposaccharide phosphate mimetics, and (e) submicron emulsions comprising a metabolizable oil, such as squalene, and an emulsifying agent, such as one or more sorbitan derivatives (e.g., MF59).

Still other supplementary components can be included within the various compositions of the present invention, including pharmaceuticals, hormones, enzymes, transcription or translation mediators, metabolic pathway intermediates, immunomodulators, and combinations thereof.

Further embodiments of the invention are directed to methods of delivering antigens to a host animal, which comprises administering to the host animal any of the immunogenic compositions described herein. The host animal is preferably a vertebrate animal, more preferably a mammal, and even more preferably a human.

The present invention is also directed to methods of stimulating an immune response in a host animal, comprising administering to the animal any of the immunogenic compositions described herein in an amount effective to induce the immune response.

The present invention is further directed to methods of immunizing a host animal against a tumor or a pathogenic organism comprising administering to the animal any of the immunogenic compositions described herein in an amount effective to induce a protective response.

Delivery of the immunogenic compositions of the invention may be performed by any known method, including direct injection (e.g., subcutaneously, intraperitoneally, intravenously or intramuscularly).

Hence, according to some embodiments of the present invention, compositions and methods are provided which treat, including prophylactically and/or therapeutically immunize, a host animal against viral, bacterial, fungal, mycoplasma, or protozoan infections, as well as against tumors. The methods of the present invention are useful for conferring prophylactic and/or therapeutic immunity to a host animal, preferably a human.

Other embodiments of the present invention are directed to methods for producing the above compositions. For example, the above polymer microparticles can be produced by a method that comprises: (a) forming a water-in-oil-in-water emulsion comprising water, organic solvent, biodegradable polymer; (b) removing the organic solvent from the emulsion, to form the polymer microparticles; and (c) adsorbing a toxoid antigen, such as a tetanus or diphtheria toxoid, a polysaccharide containing antigen, such as a Hib, meningococcal or pneumococcal polysaccharide or conjugate antigen, or a combination thereof, to the microparticles. In many embodiments the emulsion will further comprise a surfactant, for example, an anionic surfactant.

One advantage of the immunogenic compositions of the present invention is the ability to generate immune responses in a vertebrate subject, including conventional antibody responses.

These and various other embodiments, aspects and advantages of the present invention will become readily apparent to those of ordinary skill in the art in view of the disclosure herein and the appended claims.

DETAILED DESCRIPTION OF THE INVENTION

Figure 1:
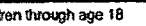
FIG. 1 is the Recommended Childhood and Adolescent Immunization Schedule United States 2003, from the U.S. Department of Health and Human Services, Centers for Disease Control and Prevention, National Immunization Program. This schedule indicates the recommended ages for routine administration of currently licensed childhood vaccines, as of Dec. 1, 2002, for children through age 18 years. Any dose not given at the recommended age should be given at any subsequent visit when indicated and feasible. The hatched areas indicate age groups that warrant special effort to administer those vaccines not previously given. Additional vaccines may be licensed and recommended during the year. Licensed combination vaccines may be used whenever any components of the combination are indicated and the vaccine's other components are not contraindicated. Providers should consult the manufacturers' package inserts for detailed recommendations.
Figure 2:
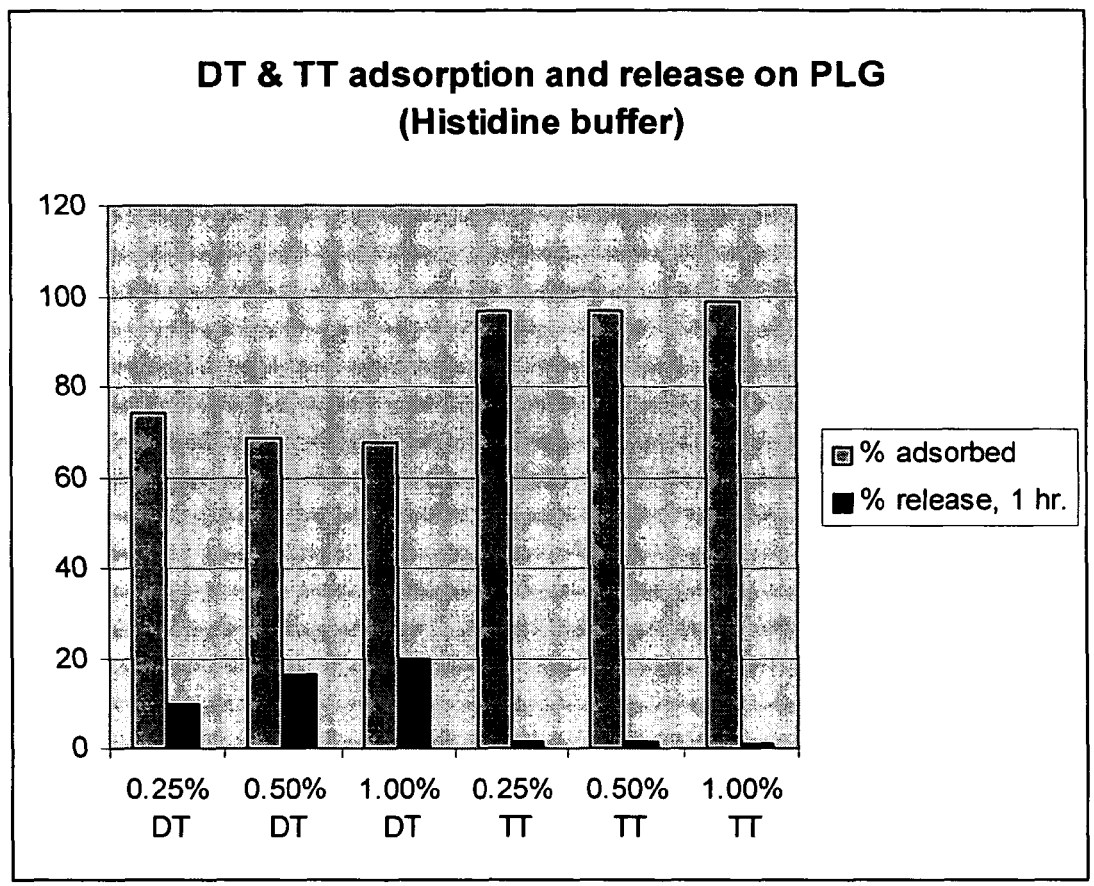
FIG. 2 is a bar graph illustrating % adsorption and % release for tetanus toxoid and diphtheria toxoid from PLG particles in Histidine buffer.

The practice of the present invention will employ, unless otherwise indicated, conventional methods of chemistry, polymer chemistry, biochemistry, molecular biology, immunology and pharmacology, within the skill of the art. Such techniques are explained fully in the literature. See, e.g., *Remington's Pharmaceutical Sciences,* 18th Edition (Easton, Pa.: Mack Publishing Company, 1990); *Methods In Enzymology* (S. Colowick and N. Kaplan, eds., Academic Press, Inc.); *Handbook of Experimental Immunology*, Vols. I-IV (D. M. Weir and C. C. Blackwell, eds., 1986, Blackwell Scientific Publications); Sambrook, et al., *Molecular Cloning: A Laboratory Manual* (2nd Edition, 1989); *Handbook of Surface and Colloidal Chemistry* (Birdi, K. S., ed, CRC Press, 1997) and *Seymour/Carraher=s Polymer Chemistry* (4th edition, Marcel Dekker Inc., 1996).

All publications, patents and patent applications cited herein, whether supra or infra, are hereby incorporated by reference in their entirety.

As used in this specification and any appended claims, the singular forms "a," "an" and "the" include plural references unless the content clearly dictates otherwise. Thus, for example, the term "microparticle" refers to one or more microparticles, and the like.

Unless the context indicates otherwise, all percentages and ratios herein are given on a weight basis.

A. Definitions

In describing the present invention, the following terms will be employed, and are intended to be defined as indicated below.

The term "microparticle" as used herein, refers to a particle of about 10 nm to about 150 μm in diameter, more typically about 200 nm to about 30 μM in diameter, and even more typically about 500 nm to about 10-20 μm in diameter. The microparticles of the present invention may aggregate into larger masses under some circumstances. The microparticle will generally be of a diameter that permits parenteral or mucosal administration without occluding needles and capillaries. Microparticle size is readily determined by techniques well known in the art, such as photon correlation spectroscopy, laser diffractometry and/or scanning electron microscopy. The term "particle" may also be used to denote a microparticle as defined herein.

Polymer microparticles for use herein are typically formed from materials that are sterilizable, substantially non-toxic, and biodegradable. Such materials include poly(α-hydroxy acids), polyhydroxybutyric acids, polycaprolactones, polyorthoesters, polyanhydrides, and polycyanoacrylates (e.g., polyalkylcyanoacrylate or "PACA"). More typically, microparticles for use with the present invention are polymer microparticles derived from poly(α-hydroxy acids), for example, from a poly(lactide) ("PLA") or a copolymer of lactide and glycolide, such as a poly(D,L-lactide-co-glycolide) ("PLG"), or a copolymer of D,L-lactide and caprolactone. The polymer microparticles may be derived from any of various polymeric starting materials which have a variety of molecular weights and, in the case of the copolymers such as PLG, a variety of monomer (e.g., lactide:glycolide) ratios, the selection of which will be largely a matter of choice, depending in part on the coadministered species. These parameters are discussed further below.

The term "surfactant" as used herein includes detergents, dispersing agents, suspending agents, and emulsion stabilizers. Cationic surfactants include, but are not limited to, cetyltrimethylammonium bromide or "CTAB" (e.g., cetrimide), benzalkonium chloride, DDA (dimethyl dioctodecyl ammonium bromide), DOTAP (dioleoyl-3-trimethylammonium-propane), and the like. Anionic surfactants include, but are not limited to, SDS (sodium dodecyl sulfate), SLS (sodium lauryl sulfate), DSS (disulfosuccinate), sulphated fatty alcohols, and the like. Nonionic surfactants include, but are not limited to, PVA, povidone (also known as polyvinylpyrrolidone or PVP), sorbitan esters, polysorbates, polyoxyethylated glycol monoethers, polyoxyethylated alkyl phenyls, poloxamers, and the like.

The term "submicron emulsion" as used herein refers to an oil-in-water emulsion comprising oil droplets, substantially all of which range in size up to 1000 nm, for example, from 10 nm to 1000 nm.

The term "pharmaceutical" refers to biologically active compounds such as antibiotics, antiviral agents, growth factors, hormones, antigens and the like.

The term "adjuvant" refers to any substance that assists or modifies the action of a pharmaceutical, including but not limited to immunological adjuvants, which increase or diversify the immune response to an antigen. Hence, immunological adjuvants are compounds that are capable of potentiating an immune response to antigens.

A "polynucleotide" is a nucleic acid polymer. A polynucleotide can include as little as 5, 6, 7 or 8 nucleotides. Furthermore, a "polynucleotide" can include both double- and single-stranded sequences and refers to, but is not limited to, cDNA from viral, procaryotic or eukaryotic mRNA, genomic RNA and DNA sequences from viral (e.g. RNA and DNA viruses and retroviruses) or procaryotic DNA, and synthetic DNA sequences. The term also captures sequences that include any of the known base analogs of DNA and RNA. The term further includes modifications, such as deletions, additions and substitutions (generally conservative in nature), to a native sequence, for example, where the nucleic acid molecule encodes an antigenic protein. These modifications may be deliberate, as through site-directed mutagenesis, or may be accidental, such as through mutations of hosts that produce antigens.

As used herein, the phrase "nucleic acid" refers to DNA, RNA, or chimeras formed therefrom.

A "polynucleotide-containing species" is a molecule, at least a portion of which is a polynucleotide. Examples include RNA vector constructs, DNA vector constructs and so forth.

An "oligosaccharide" refers to a relatively short monosaccharide polymer, i.e., one containing from 2 to 30 monosaccharide units. A "polysaccharide" is a monosaccharide polymer that is beyond oligosaccharide length (i.e., one containing more than 30 monosaccharide units). Moreover, as used herein, the term "polysaccharide" also refers to a monosaccharide polymer that contain two or more linked monosaccharides. To avoid any ambiguity, the second definition is to be applied at all times, unless there are explicit indications to the contrary. The monosaccharides are typically linked by glycosidic linkages. Both full-length, naturally occurring polysaccharides and fragments thereof are encompassed by the definition. The terms also include modifications, such as deletions, additions and substitutions to a native polysaccharide sequence, for example, such that the polysaccharide maintains the ability to elicit an immunological response on a subject to which the polysaccharide is administered.

A "monosaccharide" is a polyhydric alcohol (i.e., an alcohol that further comprises either an aldehyde group (in which case the monosaccharide is an aldose) or a keto group (in which case the monosaccharide is a ketose). Monosaccharides typically contain from 3-10 carbons. Moreover, monosaccharides typically have the empirical formula $(CH_2O)_n$ where n is an integer of three or greater, typically 3-10. Examples of 3-6 carbon aldoses include glyceraldehyde, erythrose, threose, ribose, 2-deoxyribose, arabinose, xylose, lyxose, allose, altrose, glucose, mannose, gulose, idose, galactose, and talose. Examples of 3-6 carbon ketoses include dihydroxyacetone, erythrulose, ribulose, xylulose, psicose, fructose, sorbose, and tagatose. Naturally occurring monosaccharides are normally found in the D-isomer form, as opposed to the L-form.

As used herein the term "saccharide" encompasses monosaccharides, oligosaccharides and polysaccharides. A "saccharide-containing species" is a molecule, at least a portion of which is a saccharide. Examples include saccharide antigens, antigens comprising saccharides conjugated to carrier peptides, and so forth.

The terms "polypeptide" and "protein" refer to a polymer of amino acid residues and are not limited to a minimum length of the product. Thus, peptides, oligopeptides, dimers, multimers, and the like, are included within the definition. Both full-length proteins and fragments thereof are encompassed by the definition. The terms also include modifications, such as deletions, additions and substitutions (generally conservative in nature), to a native sequence, for example, such that the protein maintains the ability to elicit an immunological response or have a therapeutic effect on a subject to which the protein is administered.

A "polypeptide-containing species" is a molecule, at least a portion of which is a polypeptide. Examples include polypeptides, proteins including glycoproteins, saccharide antigens conjugated to carrier proteins, and so forth.

By "antigen" is meant a molecule that contains one or more epitopes capable of stimulating a host's immune system to make a cellular antigen-specific immune response when the antigen is presented, or a humoral antibody response. An antigen may be capable of eliciting a cellular and/or humoral response by itself or when present in combination with another molecule.

An "epitope" is that portion of an antigenic molecule or antigenic complex that determines its immunological specificity. An epitope is within the scope of the present definition of antigen. Commonly, an epitope is a polypeptide or polysaccharide in a naturally occurring antigen. In artificial antigens, it can be a low molecular weight substance such as an arsanilic acid derivative. An epitope will react specifically in vivo or in vitro with, for example, homologous antibodies or T lymphocytes. Alternative descriptors are antigenic determinant, antigenic structural grouping and haptenic grouping.

A polypetide epitope can include, for example, between about 5-15 amino acids. Epitopes of a given antigen can be identified using any number of epitope mapping techniques, well known in the art. See, e.g., *Epitope Mapping Protocols* in Methods in Molecular Biology, Vol. 66 (Glenn E. Morris, Ed., 1996) Humana Press, Totowa, N.J. For example, linear epitopes may be determined by, for example, concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al. (1984) *Proc. Natl. Acad. Sci. USA* 81:3998-4002; Geysen et al. (1986) *Molec. Immunol.* 23:709-715. Similarly, conformational epitopes are readily identified by determining spatial conformation of amino acids such as by, e.g., x-ray crystallography and 2-dimensional nuclear magnetic resonance. See, e.g., *Epitope Mapping Protocols*, supra.

The term "antigen" as used herein denotes both subunit antigens, i.e., antigens which are separate and discrete from a whole organism with which the antigen is associated in nature, as well as killed, attenuated or inactivated bacteria, viruses, parasites or other pathogens or tumor cells. Antibodies such as anti-idiotype antibodies, or fragments thereof, and synthetic peptide mimotopes, which can mimic an antigen or antigenic determinant, are also captured under the definition of antigen as used herein.

Similarly, an oligonucleotide or polynucleotide (oligonucleotides are polynucleotides of relatively low molecular weight, typically containing from 2 to 100 nucleotides) that expresses an immunogenic protein, or antigenic determinant in vivo, such as in nucleic acid immunization applications, is also included in the definition of antigen herein.

Furthermore, for purposes of the present invention, an "antigen" refers to a protein, which includes modifications, such as deletions, additions and substitutions (generally conservative in nature), to the native sequence, as long as the protein maintains the ability to elicit an immunological response. These modifications may be deliberate, as through site-directed mutagenesis, or may be accidental, such as through mutations of hosts which produce the antigens.

An "immunological response" to an antigen or composition is the development in a subject of a humoral and/or a cellular immune response to molecules present in the composition of interest. For purposes of the present invention, a "humoral immune response" refers to an immune response mediated by antibody molecules, while a "cellular immune response" is one mediated by T-lymphocytes and/or other white blood cells. One important aspect of cellular immunity involves an antigen-specific response by cytolytic T-cells ("CTLs"). CTLs have specificity for peptide antigens that are presented in association with proteins encoded by the major histocompatibility complex (MHC) and expressed on the surfaces of cells. CTLs help induce and promote the intracellular destruction of intracellular microbes, or the lysis of cells infected with such microbes. Another aspect of cellular immunity involves an antigen-specific response by helper T-cells. Helper T-cells act to help stimulate the function, and focus the activity of, nonspecific effector cells against cells displaying peptide antigens in association with MHC molecules on their surface. A "cellular immune response" also refers to the production of cytokines, chemokines and other such molecules produced by activated T-cells and/or other white blood cells, including those derived from CD4+ and CD8+ T-cells. A composition such as an immunogenic composition or vaccine that elicits a cellular immune response may serve to sensitize a vertebrate subject by the presentation of antigen in association with MHC molecules at the cell surface. The cell-mediated immune response is directed at, or near, cells presenting antigen at their surface. In addition, antigen-specific T-lymphocytes can be generated to allow for the future protection of an immunized host. The ability of a particular antigen or composition to stimulate a cell-mediated immunological response may be determined by a number of assays, such as by lymphoproliferation (lymphocyte activation) assays, CTL cytotoxic cell assays, by assaying for T-lymphocytes specific for the antigen in a sensitized subject, or by measurement of cytokine production by T cells in response to restimulation with antigen. Such assays are well known in the art. See, e.g., Erickson et al., *J. Immunol.* (1993) 151:4189-4199; Doe et al., *Eur. J. Immunol.* (1994) 24:2369-2376. The antigen of interest may also elicit an antibody-mediated immune response. Hence, an immunological response may include one or more of the following effects: the production of antibodies by B-cells; and/or the activation of suppressor T-cells and/or γδ T-cells directed specifically to an antigen or antigens present in the composition or vaccine of interest. These responses may serve to neutralize infectivity, and/or mediate antibody-complement, or antibody dependent cell cytotoxicity (ADCC) to provide protection to an immunized host. Such responses can be determined using standard immunoassays and neutralization assays, well known in the art, for instance, radioimmunoassays and ELISAs.

The immunogenic compositions of the present invention display "enhanced immunogenicity" when they possess a greater capacity to elicit an immune response than the immune response elicited by an equivalent amount of the antigen in a differing composition. Thus, a composition may display "enhanced immunogenicity," for example, because the composition generates a stronger immune response, or because a lower dose of antigen is necessary to achieve an immune response in the subject to which it is administered. Such enhanced immunogenicity can be determined, for example, by administering the compositions of the invention, and antigen controls, to animals and comparing assay results of the two.

As used herein, "treatment" (including variations thereof, for example, "treat" or "treated") refers to any of (i) the prevention of a pathogen or disorder in question (e.g. cancer or a pathogenic infection, as in a traditional vaccine), (ii) the reduction or elimination of symptoms, and (iii) the substantial or complete elimination of the pathogen or disorder in question. Treatment may be effected prophylactically (prior to arrival of the pathogen or disorder in question) or therapeutically (following arrival of the same).

The terms "effective amount" or "pharmaceutically effective amount" of an immunogenic composition of the present invention refer herein to a sufficient amount of the immunogenic composition to treat a condition of interest. The exact amount required will vary from subject to subject, depending, for example, on the species, age, and general condition of the subject; the severity of the condition being treated; the particular antigen of interest; in the case of an immunological response, the capacity of the subject's immune system to synthesize antibodies, for example, and the degree of protection desired; and the mode of administration, among other factors. An appropriate "effective" amount in any individual case may be determined by one of ordinary skill in the art. Thus, a "therapeutically effective amount" will typically fall in a relatively broad range that can be determined through routine trials.

By "vertebrate subject" or "vertebrate animal" is meant any member of the subphylum cordata, including, without limitation, mammals such as cattle, sheep, pigs, goats, horses, and humans; domestic animals such as dogs and cats; and birds, including domestic, wild and game birds such as cocks and hens including chickens, turkeys and other gallinaceous birds. The term does not denote a particular age. Thus, both adult and newborn animals are covered.

By "pharmaceutically acceptable" or "pharmacologically acceptable" is meant a material which is not biologically or otherwise undesirable, i.e., the material may be administered to an individual without causing any excessively undesirable biological effects in the individual or interacting in an excessively deleterious manner with any of the components of the composition in which it is contained.

The term "excipient" refers to any essentially accessory substance that may be present in the finished dosage form. For example, the term "excipient" includes vehicles, binders, disintegrants, fillers (diluents), lubricants, glidants (flow enhancers), compression aids, colors, sweeteners, preservatives, suspending/dispersing agents, film formers/coatings, flavors and printing inks.

By "physiological pH" or a "pH in the physiological range" is meant a pH in the range of approximately 7.2 to 8.0 inclusive, more typically in the range of approximately 7.2 to 7.6 inclusive.

As used herein, the phrase "vector construct" generally refers to any assembly that is capable of directing the expression of a nucleic acid sequence(s) or gene(s) of interest. A vector construct typically includes transcriptional promoter/enhancer or locus defining element(s), or other elements which control gene expression by other means such as alternate splicing, nuclear RNA export, post-translational modification of messenger, or post-transcriptional modification of protein. In addition, the vector construct typically includes a sequence which, when transcribed, is operably linked to the sequence(s) or gene(s) of interest and acts as a translation initiation sequence. The vector construct may also optionally include a signal that directs polyadenylation, a selectable marker, as well as one or more restriction sites and a translation termination sequence. In addition, if the vector construct is placed into a retrovirus, the vector construct may include a packaging signal, long terminal repeats (LTRs), and positive and negative strand primer binding sites appropriate to the retrovirus used (if these are not already present).

A "DNA vector construct" refers to a DNA molecule that is capable of directing the expression of a nucleic acid sequence(s) or gene(s) of interest.

One specific type of DNA vector construct is a plasmid, which is a circular episomal DNA molecule capable of autonomous replication within a host cell. Typically, a plasmid is a circular double stranded DNA loop into which additional DNA segments can be ligated. pCMV is one specific plasmid that is well known in the art. A preferred pCMV vector is one which contains the immediate-early enhancer/promoter of CMV and a bovine growth hormone terminator. It is described in detail in Chapman, B. S., et al. 1991. "Effect of intron A from human cytomegalovirus (Towne) immediate-early gene on heterologous expression in mammalian cells." Nucleic Acids Res. 19:3979-86.

Other DNA vector constructs are known, which are based on RNA viruses. These DNA vector constructs typically comprise a promoter that functions in a eukaryotic cell, 5' of a cDNA sequence for which the transcription product is an RNA vector construct (e.g., an alphavirus RNA vector replicon), and a 3' termination region. The RNA vector construct preferably comprises an RNA genome from a picornavirus, togavirus, flavivirus, coronavirus, paramyxovirus, yellow fever virus, or alphavirus (e.g., Sindbis virus, Semliki Forest virus, Venezuelan equine encephalitis virus, or Ross River virus), which has been modified by the replacement of one or more structural protein genes with a selected heterologous nucleic acid sequence encoding a product of interest. The RNA vector constructs can be obtained by transcription in vitro from a DNA template. Specific examples include Sindbis-virus-based plasmids (PSIN) such as pSINCP, described, for example, in U.S. Pat. Nos. 5,814,482 and 6,015,686, as well as in International Patent Applications WO 97/38087, WO 99/18226 and commonly owned WO 02/26209. The construction of such vectors, in general, is described in U.S. Pat. Nos. 5,814,482 and 6,015,686.

Other examples of vector constructs include RNA vector constructs (e.g., alphavirus vector constructs) and the like. As used herein, "RNA vector construct", "RNA vector replicon" and "replicon" refer to an RNA molecule that is capable of directing its own amplification or self-replication in vivo, typically within a target cell. The RNA vector construct is used directly, without the requirement for introduction of DNA into a cell and transport to the nucleus where transcription would occur. By using the RNA vector for direct delivery into the cytoplasm of the host cell, autonomous replication and translation of the heterologous nucleic acid sequence occurs efficiently.

B. General Methods

1. Microparticle Compositions

Useful polymers for forming the immunogenic microparticle compositions described herein include homopolymers, copolymers and polymer blends derived from the following: polyhydroxybutyric acid (also known as polyhydroxybutyrate); polyhydroxy valeric acid (also known as polyhydroxyvalerate); polyglycolic acid (PGA) (also known as polyglycolide); polylactic acid (PLA) (also known as polylactide); polydioxanone; polycaprolactone; polyorthoester; and polyanhydride. More typical are poly(α-hydroxy acids), such as poly(L-lactide), poly(D,L-lactide) (both referred to as APLA" herein), poly(hydoxybutyrates), copolymers of lactide and glycolide, such as poly(D,L-lactide-co-glycolides) (designated as "PLG" herein), or copolymers of D,L-lactide and caprolactone.

The above polymers are available in a variety of molecular weights, and the appropriate molecular weight for a given use is readily determined by one of skill in the art. Thus, for example, a suitable molecular weight for PLA may be on the order of about 2000 to 5000. A suitable molecular weight for PLG may range from about 10,000 to about 200,000, typically about 15,000 to about 150,000.

Where copolymers are used, copolymers with a variety of monomer ratios may be available. For example, where PLG is used to form the microparticles, a variety of lactide:glycolide molar ratios will find use herein, and the ratio is largely a matter of choice, depending in part on any coadministered adsorbed and/or entrapped species and the rate of degradation desired. For example, a 50:50 PLG polymer, containing 50% D,L-lactide and 50% glycolide, will provide a fast resorbing copolymer while 75:25 PLG degrades more slowly, and 85:15 and 90:10, even more slowly, due to the increased lactide component. Mixtures of microparticles with varying lactide:glycolide ratios may also find use herein in order to achieve desired release kinetics. Degradation rate of the microparticles of the present invention can also be controlled by such factors as polymer molecular weight and polymer crystallinity.

PLG copolymers with varying lactide:glycolide ratios and molecular weights are readily available commercially from a number of sources including from Boehringer Ingelheim, Germany and Birmingham Polymers, Inc., Birmingham, Ala. Some exemplary PLG copolymers include: (a) RG 502, a PLG having a 50:50 lactide/glycolide molar ratio and a molecular weight of 12,000 Da; (b) RG 503, a PLG having a 50:50 lactide/glycolide molar ratio and a molecular weight of 34,000 Da; (c) RG 504, a PLG having a 50:50 lactide/glycolide molar ratio and a molecular weight of 48,000 Da, (d) RG 752, a PLG having a 75:25 lactide/glycolide molar ratio and a molecular weight of 22,000 Da; and (e) RG 755, a PLG having a 75:25 lactide/glycolide molar ratio and a molecular weight of 68,000 Da. PLG polymers can also be synthesized by simple polycondensation of the lactic acid component using techniques well known in the art, such as described in Tabata et al., *J. Biomed. Mater. Res.* (1988) 22:837-858.

Where used, poly(D,L-lactide-co-glycolide) polymers are typically those having a molar lactide/glycolide molar ratio ranging from 20:80 to 80:20, more typically 40:60 to 60:40, and having a molecular weight ranging from 10,000 to 100,000 Daltons, more typically from 20,000 Daltons to 70,000 Daltons.

Microparticles are prepared using any of several methods well known in the art. For example, in some embodiments, double emulsion/solvent evaporation techniques, such as those described in U.S. Pat. No. 3,523,907 and Ogawa et al., *Chem. Pharm. Bull.* (1988) 36:1095-1103, can be used herein to make the microparticles. These techniques involve the formation of a primary emulsion consisting of droplets of polymer solution, which is subsequently mixed with a continuous aqueous phase containing a particle stabilizer/surfactant.

In other embodiments, microparticles can also be formed using spray-drying and coacervation as described in, e.g., Thomasin et al., *J. Controlled Release* (1996) 41:131; U.S. Pat. No. 2,800,457; Masters, K. (1976) *Spray Drying* 2nd Ed. Wiley, New York; air-suspension coating techniques, such as pan coating and Wurster coating, as described by Hall et al., (1980) The AWurster Process@ in *Controlled Release Technologies: Methods, Theory, and Applications* (A. F. Kydonieus, ed.), Vol. 2, pp. 133-154 CRC Press, Boca Raton, Fla. and Deasy, P. B., *Crit. Rev. Ther. Drug Carrier Syst.* (1988) S(2):99-139; and ionic gelation as described by, e.g., Lim et al., *Science* (1980) 210:908-910.

In preferred embodiments, a water-in-oil-in-water (w/o/w) solvent evaporation system can be used to form the microparticles, along the lines described by O'Hagan et al., *Vaccine* (1993) 11:965-969, PCT/US99/17308 (WO 00/06123) to O'Hagan et al. and Jeffery et al., *Pharm. Res.* (1993) 10:362.

In general, a polymer of interest such as PLG is dissolved in an organic solvent, such as ethyl acetate, dimethylchloride (also called methylene chloride and dichloromethane), acetonitrile, acetone, chloroform, and the like. The polymer will typically be provided in about a 1-30%, more typically about a 2-15%, even more typically about a 3-10% and most typically, about a 4-8% solution, in organic solvent. The polymer solution is then combined with a first volume of aqueous solution and emulsified to form an o/w emulsion. The aqueous solution can be, for example, deionized water, normal saline, a buffered solution, for example, phosphate-buffered saline (PBS) or a sodium citrate/ethylenediaminetetraacetic acid (sodium citrate/ETDA) buffer solution. The latter solutions can (a) provide a tonicity, i.e., osmolality, that is essentially the same as normal physiological fluids and (b) maintain a pH compatible with normal physiological conditions. Alternatively, the tonicity and/or pH characteristics of the compositions of the present invention can be adjusted after microparticle formation and prior to administration. Preferably, the volume ratio of polymer solution to aqueous solution ranges from about 5:1 to about 20:1, more preferably about 10:1. Emulsification is conducted using any equipment appropriate for this task, and is typically a high-shear device such as, e.g., a homogenizer.

In some embodiments, one or more additional components are entrapped within the microparticles. For example, additional antigen, and/or the supplemental components described below can be introduced by adding the same (a) to the polymer solution, if in oil-soluble or oil-dispersible form or (b) to the aqueous solution, if in water-soluble or water-dispersible form.

A volume of the o/w emulsion is then combined with a larger second volume of an aqueous solution, which typically contains a surfactant. The volume ratio of aqueous solution to o/w emulsion typically ranges from about 2:1 to 10:1, more typically about 4:1. Examples of surfactants appropriate for the practice of the invention are listed above. Those of ordinary skill in the art may readily select surfactants appropriate for the type of species to be adsorbed. For example, microparticles manufactured in the presence of charged surfactants, such as anionic or cationic surfactants, may yield microparticles with a surface having a net negative or a net positive charge, which can adsorb a wide variety of molecules. For example, microparticles manufactured with anionic surfactants, such as sodium dodecyl sulfate (SDS), e.g., SDS-PLG microparticles, adsorb positively charged species, for example, polypeptide-containing species such as proteins. Similarly, microparticles manufactured with cationic surfactants, such as CTAB, e.g., PLG/CTAB microparticles, adsorb negatively charged species, for example, polynucleotide-containing species such as DNA. Where the species to be adsorbed have regions of positive and negative charge, either cationic or anionic or nonionic surfactants may be appropriate. Certain species may adsorb more readily to microparticles having a combination of surfactants. Moreover, in some instances, it may be desirable to add surfactant to the above organic solution.

Where a cationic surfactant such as CTAB is used, it is typically provided in about a 0.00025-1% solution, more typically about a 0.0025-0.1% solution. Where an anionic surfactant such as DSS is used, it is typically provided in about a 0.00001-0.025% solution, more typically about a 0.0001-0.0025% solution. Where a nonionic surfactant such as PVA is used, it is typically provided in about a 2-15% solution, more typically about a 4-10% solution. For a cationic surfactant, a weight-to-weight surfactant-to-polymer ratio in the range of from about 0.00001:1 to about 0.5:1 is typically used; more typically from about 0.001:1 to about 0.1:1, and even more typically from about 0.0025:1 to about 0.05:1; for an anionic surfactant such as DSS, a weight-to-weight surfactant-to-polymer ratio in the range of from about 0.00001:1 to about 0.025:1 is typically used, more typically from about 0.0001:1 to about 0.0025:1; for a nonionic surfactant such as PVA a weight-to-weight surfactant-to-polymer ratio in the range of from about 0.001:1 to about 0.1:1 is typically used, more typically from about 0.0025:1 to about 0.05:1 is used.

This mixture is then homogenized to produce a stable w/o/w double emulsion. Each of the above homogenization steps is typically conducted at a room temperature (i.e., 25° C.) or less, more typically, for example, while cooling within an ice bath.

Organic solvents are then evaporated. Following preparation, microparticles can be used as is or, for example, lyophilized for future use.

The formulation parameters can be manipulated to allow the preparation of small microparticles on the order of 0.05 µm (50 nm) to larger microparticles 50 µm or even larger. See, e.g., Jeffery et al., *Pharm. Res.* (1993) 10:362-368; McGee et al., *J. Microencap.* (1996). For example, reduced agitation typically results in larger microparticles, as do an increase in internal phase volume and an increase in polymer concentration. Small particles are typically produced by increased agitation as well as low aqueous phase volumes, high concentrations of emulsion stabilizers and a decrease in polymer concentration.

Particle size can be determined by, e.g., laser light scattering, using for example, a spectrometer incorporating a helium-neon laser. Generally, particle size is determined at room temperature and involves multiple analyses of the sample in question (e.g., 5-10 times) to yield an average value for the particle diameter. Particle size is also readily determined using scanning electron microscopy (SEM).

Upon preparation, a variety of components can be admixed with the microparticles, including toxoid antigen and/or polysaccharide-containing antigen, any additional antigens, and any supplemental components such as those described below, and the resulting formulation can be lyophilized prior to use if desired. Typically, theses components are added to the microparticles as an aqueous solution or dispersion. In some instances, these species will become adsorbed to the surface of the microparticles (see, e.g., the Examples below in which toxoid antigens are adsorbed to the microparticle surface). The content of the adsorbed species can be determined using standard techniques.

Thus, the polymer microparticles of the present invention may have a variety of components adsorbed thereon, as well as having a variety of components entrapped or encapsulated within them. For example, one of ordinary skill in the art may prepare in accordance with the invention microparticles having adsorbed antigens and/or immunological adjuvants, in addition to adsorbed toxoid antigen and/or polysaccharide-containing antigen. One of ordinary skill in the art may also prepare, in accordance with the invention, microparticles having encapsulated components, such as antigens and/or immunological adjuvants, in addition to adsorbed toxoid antigen and/or polysaccharide containing antigen.

2. Antigens

The present invention utilizes numerous antigens including toxoid antigens from tetanus toxoid, diphtheria toxoid, or both. A toxoid is a toxin that has been treated so as to reduce or eliminate its toxicity, while retaining adequate immunogenicity. Toxoids are commonly made by treating toxins produced by a bacterium that causes disease with heat and/or chemicals. For example, purified diphtheria and tetanus toxoids are available commercially, which have been prepared by formalin treatment of *Corynebacterium diphtheriae* and *Clostridium tetani* exotoxins, respectively.

The present invention will also find use for stimulating an immune response against a wide variety of antigens in addition to toxoid antigens.

For example, antigens from the hepatitis family of viruses, including hepatitis A virus (HAV), hepatitis B virus (HBV), hepatitis C virus (HCV), the delta hepatitis virus (HDV), hepatitis E virus (HEV) and hepatitis G virus (HGV), can be conveniently used in the techniques described herein. By way of example, the viral genomic sequence of HCV is known, as are methods for obtaining the sequence. See, e.g., International Publication Nos. WO 89/04669; WO 90/11089; and WO 90/14436. The HCV genome encodes several viral proteins, including E1 (also known as E) and E2 (also known as E2/NSI) and an N-terminal nucleocapsid protein (termed "core") (see, Houghton et al., *Hepatology* (1991) 14:381-388, for a discussion of HCV proteins, including E1 and E2). Each of these proteins, as well as antigenic fragments thereof, will find use in the present composition and methods.

Similarly, the sequence for the δ-antigen from HDV is known (see, e.g., U.S. Pat. No. 5,378,814) and this antigen can also be conveniently used in the present composition and methods. Additionally, antigens derived from HBV, such as the core antigen, the surface antigen, sAg, as well as the presurface sequences, pre-S1 and pre-S2 (formerly called pre-S), as well as combinations of the above, such as sAg/pre-S 1, sAg/pre-S2, sAg/pre-S1/pre-S2, and pre-S1/pre-S2, will find use herein. See, e.g., AHBV Vaccines—from the laboratory to license: a case study@ in Mackett, M. and Williamson, J. D., *Human Vaccines and Vaccination*, pp. 159-176, for a discussion of HBV structure; and U.S. Pat. Nos. 4,722,840, 5,098,704, 5,324,513, incorporated herein by reference in their entireties; Beames et al., *J. Virol.* (1995) 69:6833-6838, Birnbaum et al., *J. Virol.* (1990) 64:3319-3330; and Zhou et al., *J. Virol.* (1991) 65:5457-5464.

Antigens from the herpesvirus family, including proteins derived from herpes simplex virus (HSV) types 1 and 2, such as HSV-1 and HSV-2 glycoproteins gB, gD and gH; antigens derived from varicella zoster virus (VZV), Epstein-Barr virus (EBV) and cytomegalovirus (CMV) including CMV gB and gH; and antigens derived from other human herpesviruses such as HHV6 and HHV7 can also be conveniently used in connection with the present invention. (See, e.g. Chee et al., *Cytomegaloviruses* (J. K. McDougall, ed., Springer-Verlag 1990) pp. 125-169, for a review of the protein coding content of cytomegalovirus; McGeoch et al., *J. Gen. Virol.* (1988) 69:1531-1574, for a discussion of the various HSV-1 encoded proteins; U.S. Pat. No. 5,171,568 for a discussion of HSV-1 and HSV-2 gB and gD proteins and the genes encoding therefor; Baer et al., *Nature* (1984) 310:207-211, for the identification of protein coding sequences in an EBV genome; and Davison and Scott, *J. Gen. Virol.* (1986) 67:1759-1816, for a review of VZV.)

Antigens derived from other viruses will also find use in the compositions and methods of the present invention, such as without limitation, proteins from members of the families Picornaviridae (e.g., polioviruses, etc.); Caliciviridae; Togaviridae (e.g., rubella virus, dengue virus, etc.); Flaviviridae; Coronaviridae; Reoviridae; Birnaviridae; Rhabodoviridae (e.g., rabies virus, etc.); Filoviridae; Paramyxoviridae (e.g., mumps virus, measles virus, respiratory syncytial virus, etc.); Orthomyxoviridae (e.g., influenza virus types A, B and C, etc.); Bunyaviridae; Arenaviridae; Retroviridae (e.g., HTLV-I; HTLV-II; HIV-1 (also known as HTLV-III, LAV, ARV, hTLR, etc.)), including but not limited to antigens from the isolates $HIV_{IIIb}$, $HIV_{SF2}$, $HIV_{LAV}$, $HIV_{LAI}$, $HIV_{MN}$); $HIV-1_{CM235}$, $HIV-1_{US4}$; HIV-2; simian immunodeficiency virus (SIV) among others. Additionally, antigens may also be derived from human papillomavirus (HPV) and the tick-borne encephalitis viruses. See, e.g. Virology, 3rd Edition (W. K. Joklik ed. 1988); *Fundamental Virology*, 2nd Edition (B. N. Fields and D. M. Knipe, eds. 1991), for a description of these and other viruses.

More particularly, the gp120 or gp140 envelope proteins from any of the above HIV isolates, including members of the various genetic subtypes of HIV, are known and reported (see, e.g., Myers et al., Los Alamos Database, Los Alamos National Laboratory, Los Alamos, N.M. (1992); Myers et al., *Human Retroviruses and Aids,* 1990, Los Alamos, N.M.: Los Alamos National Laboratory; and Modrow et al., *J. Virol.* (1987) 61:570-578, for a comparison of the envelope sequences of a variety of HIV isolates) and antigens derived from any of these isolates will find use in the present methods. Furthermore, the invention is equally applicable to other immunogenic proteins derived from any of the various HIV isolates, including any of the various envelope proteins such as gp160 and gp41, gag antigens such as p24gag and p55gag, as well as proteins derived from the pol and tat regions.

Influenza virus is another example of a virus for which the present invention will be particularly useful. Specifically, the envelope glycoproteins HA and NA of influenza A are of particular interest for generating an immune response. Numerous HA subtypes of influenza A have been identified (Kawaoka et al., *Virology* (1990) 179:759-767; Webster et al., "Antigenic variation among type A influenza viruses," p. 127-168. In: P. Palese and D. W. Kingsbury (ed.), *Genetics of influenza viruses*. Springer-Verlag, New York). Thus, proteins derived from any of these isolates can also be used in the compositions and methods described herein.

The compositions and methods described herein will also find use with numerous bacterial antigens, such as those derived from organisms that cause diphtheria (further discussed above), cholera, anthrax, tuberculosis, tetanus (further discussed above), pertussis, meningitis, and other pathogenic states, including, without limitation, *Bordetella pertussis, Neisseria meningitides* (A, B, C, Y), *Neisseria gonorrhoeae, Helicobacter pylori,* and *Haemophilus influenza. Hemophilus influenza* type B (HIB), *Helicobacter pylori,* and combinations thereof. Examples of antigens from *Neisseria meningitides* B are disclosed in the following co-owned patent applications: PCT/US99/09346; PCT IB98/01665; and PCT IB99/00103. Examples of parasitic antigens include those derived from organisms causing malaria and Lyme disease.

Further antigens include antigens directed to plague, Rocky Mountain spotted fever, smallpox, typhoid, typhus, feline leukemia virus, and yellow fever.

Additional antigens for use with the invention, which are not necessarily exclusive of those listed elsewhere in this application, include the following: (a) a protein antigen from *N. meningitidis* serogroup B, such as those in Refs. 1 to 7 below; (b) an outer-membrane vesicle (OMV) preparation from *N. meningitidis* serogroup B, such as those disclosed in Refs. 8, 9, 10, 11, etc. below; (c) a saccharide antigen from *N. meningitidis* serogroup A, C, W135 and/or Y, such as the oligosaccharide disclosed in Ref. 12 below from serogroup C (see also Ref. 13); (d) a saccharide antigen from *Streptococcus pneumoniae* [e.g. Refs. 14, 15, 16]. (e) an antigen from *N. gonorrhoeae* [e.g., Refs. 1, 2, 3]; (e) an antigen from *Chlamydia pneumoniae* [e.g., Refs. 17, 18, 19, 20, 21, 22, 23]; (f) an antigen from *Chlamydia trachomatis* [e.g. Ref. 24]; (g) an antigen from hepatitis A virus, such as inactivated virus [e.g., Refs. 25, 26]; (h) an antigen from hepatitis B virus, such as the surface and/or core antigens [e.g., Refs. 26, 27]; (i) an antigen from hepatitis C virus [e.g. Ref. 28]; (j) an antigen from *Bordetella pertussis,* such as pertussis holotoxin (PT) and filamentous haemaglutinin (FHA) from *B. pertussis,* optionally also in combination with pertactin and/or agglutinogens 2 and 3 [e.g., Refs. 29 & 30]; (k) a diphtheria antigen, such as diphtheria toxoid [e.g., chapter 3 of Ref. 31] e.g. the $CRM_{197}$ mutant [e.g., Ref. 32] (further discussed above); (l) a tetanus antigen, such as a tetanus toxoid [e.g., chapter 4 of Ref. 31] (further discussed above); (m) a protein antigen from *Helicobacter pylori* such as CagA [e.g. Ref. 33], VacA [e.g. Ref. 33], NAP [e.g. Ref. 34], HopX [e.g. Ref. 35], HopY [e.g. Ref. 35] and/or urease; (n) a saccharide antigen from *Haemophilus influenzae* B [e.g. Ref. 13]; (O) an antigen from *Porphyramonas gingivalis* [e.g. Ref. 36]; (p) polio antigen(s) [e.g. Refs. 37, 38] such as IPV or OPV; (q) rabies antigen(s) [e.g. Ref. 39] such as lyophilized inactivated virus [e.g. Ref. 40, Rabavert™); (r) measles, mumps and/or rubella antigens [e.g., chapters 9, 10 and 11 of Ref. 31]; (s) influenza antigen(s) [e.g. chapter 19 of Ref. 31], such as the haemagglutinin and/or neuraminidase surface proteins; (t) an antigen from *Moraxella catarrhalis* [e.g., time 41]; (u) an antigen from *Streptococcus agalactiae* (Group B *streptococcus*) [e.g. Refs. 42, 43]; (v) an antigen from *Streptococcus pyogenes* (Group A *streptococcus*) [e.g. Refs. 43,44, 45]; (w) an antigen from *Staphylococcus aureus* [e.g. Ref. 46]; and (x) compositions comprising one or more of these antigens. Where a saccharide or carbohydrate antigen is used, it is preferably conjugated to a carrier protein in order to enhance immunogenicity [e.g. Refs. 47 to 56]. Preferred carrier proteins are bacterial toxins or toxoids, such as diphtheria or tetanus toxoids. The $CRM_{197}$ diphtheria toxoid is particularly preferred. Other suitable carrier proteins include *N. meningitidis* outer membrane protein [e.g. Ref. 57], synthetic peptides [e.g. Refs. 58, 59], heat shock proteins [e.g. Ref. 60], pertussis proteins [e.g. Refs. 61, 62], protein D from *H. Influenzae* [e.g. Ref. 63], toxin A or B from *C. difficile* [e.g. Ref. 64], etc. Where a mixture comprises capsular saccharides from both serogroups A and C, it is preferred that the ratio (w/w) of MenA saccharide:MenC saccharide is greater than 1 (e.g. 2:1, 3:1, 4:1, 5:1, 10:1 or higher). Saccharides from different serogroups of *N. meningitidis* may be conjugated to the same or different carrier proteins. Any suitable conjugation reaction can be used, with any suitable linker where necessary. Toxic protein antigens may be detoxified where necessary (e.g. detoxification of pertussis toxin by chemical and/or means [Ref. 30]. See: International patent application 99/24578 [Ref. 1]; International patent application WO99/36544 [Ref. 2]; International patent application WO99/57280 [Ref. 3]; International patent application WO00/22430 [Ref. 4]; Tettelin et al., (2000) *Science* 287:1809-1815 [Ref. 5]; International patent application WO96/29412 [Ref. 6]; Pizza et al. (2000) *Science* 287:1816-1820 [Ref. 7]; International patent application PCT/IB01/00166 [Ref. 8]; Bjune et al. (1991) *Lancet* 338(8775):1093-1096 [Ref. 9]; Fukasawa et al. (1990) *Vaccine* 17:2951-2958 [Ref. 10]; Rosenqvist et al. (1998) *Dev. Biol. Stand.* 92:323-333 [Ref. 11]; Costantino et al. (1992) *Vaccine* 10:691-698 [Ref. 12]; Costantino et al. (1999) *Vaccine* 17:1251-1263 [Ref. 13]; Watson (2000) *Padiatr Infect Dis J* 19:331-332 [Ref. 14]; Rubin (2000) *Pediatr Clin North Am* 47:269-285, v [Ref. 15]; Jedrzejas (2001) *Microbiol Mol Biol Rev* 65:187-207 [Ref. 16]; International patent application filed on 3 Jul. 2001 claiming priority from GB-0016363.4 [Ref. 17]; Kalman et al. (1999) *Nature Genetics* 21 :385-389 [Ref. 18]; Read et al. (2000) *Nucleic Acids Res* 28:1397-406 [Ref. 19]; Shirai et al. (2000) *J. Infect. Dis.* 181(Suppl 3):S524-S527 [Ref. 20]; International patent application WO99/27105 [Ref. 21]; International patent application WO00/27994 [Ref. 22]; International patent application WO00/37494 [Ref. 23]; International patent application WO99/28475 [Ref. 24]; Bell (2000) *Pediatr Infect Dis J* 19:1187-1188 [Ref. 25]; Iwarson (1995) *APMIS* 103:321-326 [Ref. 26]; Gerlich et al. (1990) *Vaccine* 8 Suppl: S63-68 & 79-80 [Ref. 27]; Hsu et al. (1999) *Clin Liver Dis* 3:901-915 [Ref. 28]; Gustafsson et al. (1996) *N. Engl. J. Med.* 334:349-355 [Ref. 29]; Rappuoli et al. (1991) *TIBTECH* 9:232-238 [Ref. 30]; *Vaccines* (1988) eds. Plotkin & Mortimer. ISBN 0-7216-1946-0 [Ref. 31]; Del Guidice et al. (1998) *Molecular Aspects of Medicine* 19:1-70 [Ref. 32]; International patent application WO93/18150 [Ref. 33]; International patent application WO99/53310 [Ref. 34]; International patent application WO98/04702 [Ref. 35]; Ross et al. (2001) *Vaccine* 19:4135-4142 [Ref. 36]; Sutter et al. (2000) *Pediatr Clin North Am* 47:287-308 [Ref. 37]; Zimmerman & Spann (1999) *Am Fam Physician* 59:113-118, 125-126 [Ref. 38]; Dreesen (1997) *Vaccine* 15 Suppl:S2-6 [Ref. 39]; *MMWR Morb Mortal Wkly Rep* 1998 Jan. 16;47(1):12, 19 [Ref. 40]; McMichael (2000) *Vaccine* 19 Suppl 1:S101-107 [Ref. 41]; Schuchat (1999) *Lancet* 353(9146):51-6 [Ref. 42]; GB patent applications 0026333.5, 0028727.6 & 0105640.7 [Ref. 43]; Dale (1999) *Infect Dis Clin North Am* 13:22743, viii [Ref. 44]; Ferretti et al. (2001) *PNAS USA* 98:4658-4663 [Ref. 45]; Kuroda et al. (2001) *Lancet* 357 (9264):1225-1240; see also pages 1218-1219 [Ref. 46]; Ramsay et al. (2001) *Lancet* 357(9251):195-196 [Ref. 47]; Lindberg (1999) *Vaccine* 17 Suppl 2:S28-36 [Ref. 48]; Buttery & Moxon (2000) *J R Coll Physicians London* 34:163-168 [Ref. 49]; Ahmad & Chapnick (1999) *Infect Dis Clin North Am* 13:113-133, vii [Ref. 50]; Goldblatt (1998) *J. Med. Microbiol.* 47:563-567 [Ref. 51]; European patent 0 477 508 [Ref. 52]; U.S. Pat. No. 5,306,492 [Ref. 53]; International patent application WO98/42721 [Ref. 54]; *Conjugate Vaccines* (eds. Cruse et al.) ISBN 3805549326, particularly vol. 10:48-114 [Ref. 55]; Hermanson (1996) *Bioconjugate Techniques* ISBN: 0123423368 & 012342335X [Ref. 56]; European patent application 0372501 [Ref. 57]; European patent application 0378881 [Ref. 58]; European patent application 0427347 [Ref. 59]; International patent application WO93/17712 [Ref. 60]; International patent application WO98/58668 [Ref. 61]; European patent application 0471177 [Ref. 62]; International patent application WO00/56360 [Ref. 63]; international patent application WO00/61761 [Ref. 64].

3. Supplemental Components

The immunogenic compositions of the present invention optionally include a variety of supplemental components. Such supplemental components include: (a) pharmaceuticals such as antibiotics and antiviral agents, nonsteroidal antiinflammatory drugs, analgesics, vasodilators, cardiovascular drugs, psychotropics, neuroleptics, antidepressants, antiparkinson drugs, beta blockers, calcium channel blockers, bradykinin inhibitors, ACE-inhibitors, vasodilators, prolactin inhibitors, steroids, hormone antagonists, antihistamines, serotonin antagonists, heparin, chemotherapeutic agents, antineoplastics and growth factors, including but not limited to PDGF, EGF, KGF, IGF-1 and IGF-2, FGF, (b) hormones including peptide hormones such as insulin, proinsulin, growth hormone, GHRH, LHRH, EGF, somatostatin, SNX-111, BNP, insulinotropin, ANP, FSH, LH, PSH and hCG, gonadal steroid hormones (androgens, estrogens and progesterone), thyroid-stimulating hormone, inhibin, cholecystokinin, ACTH, CRF, dynorphins, endorphins, endothelin, fibronectin fragments, galanin, gastrin, insulinotropin, glucagon, GTP-binding protein fragments, guanylin, the leukokinins, magainin, mastoparans, dermaseptin, systemin, neuromedins, neurotensin, pancreastatin, pancreatic polypeptide, substance P, secretin, thymosin, and the like, (c) enzymes, (d) transcription or translation mediators, (e) intermediates in metabolic pathways, (f) immunomodulators, such as any of the various cytokines including interleukin-1, interleukin-2, interleukin-3, interleukin-4, and gamma-interferon, and (g) supplementary immunological adjuvants such as those described below.

Such supplemental components can be, for example, adsorbed on the surface of the microparticles, entrapped within the microparticles, dissolved or dispersed in solution while unbound to the microparticles, adsorbed to or entrapped within another group of microparticles, and so forth.

Supplementary immunological adjuvants may be used to enhance the effectiveness of the immunogenic compositions. For example, such immunological adjuvants may be administered concurrently with the immunogenic compositions of the present invention, e.g., in the same composition or in separate compositions. Alternatively, such adjuvants may be administered prior or subsequent to the immunogenic compositions of the present invention.

Supplementary immunological adjuvants include, but are not limited to: (1) aluminum salts (alum), such as aluminum hydroxide, aluminum phosphate, aluminum sulfate, etc., although it is noted that aluminum salts are associated with local reactions as discussed above and are therefore less preferred in some embodiments of the invention; (2) other oil-in water emulsion formulations (with or without other specific immunostimulating agents such as muramyl peptides (see below) or bacterial cell wall components), such as for example (a) MF59 (International Publication No. WO90/14837; Chapter 10 in *Vaccine design: the subunit an adjuvant approach*, Eds. Powell & Newman, Plenum Press 1995), containing 5% Squalene, 0.5% Tween 80, and 0.5% Span 85 (optionally containing various amounts of MTP-PE (see below), although not required) formulated into submicron particles using a microfluidizer such as Model 110Y microfluidizer (Microfluidics, Newton, Mass.), (b) SAF, containing 10% Squalane, 0.4% Tween 80, 5% pluronic-blocked polymer L121, and thr-MDP (see below) either microfluidized into a submicron emulsion or vortexed to generate a larger particle size emulsion, and (c) RibiJ adjuvant system (RAS), (Ribi Immunochem, Hamilton, Mont.) containing 2% Squalene, 0.2% Tween 80, and one or more bacterial cell wall components from the group consisting of monophosphorylipid A (MPL), trehalose dimycolate (TDM), and cell wall skeleton (CWS), preferably MPL+CWS (DetoxJ) (for a further discussion of suitable submicron oil-in-water emulsions for use herein, see commonly owned, patent application Ser. No. 09/015,736, filed on Jan. 29, 1998); (3) saponin adjuvants, such as Quil A, or QS21 (e.g., StimulonJ (Cambridge Bioscience, Worcester, Mass.)) may be used or particles generated therefrom such as ISCOMs (immunostimulating complexes), which ICOMS may be devoid of additional detergent e.g., WO00/07621; (4) Complete Freunds Adjuvant (CFA) and Incomplete Freunds Adjuvant (IFA); (5) cytokines, such as interleukins (e.g. IL-1, IL-2, IL-4, IL-5, IL-6, IL-7, IL-12 (WO99/44636), etc.), interferons (e.g. gamma interferon), macrophage colony stimulating factor (M-CSF), tumor necrosis factor (TNF), etc.; (6) phospholipid adjuvants, including lipopolysaccharide and liposaccharide phosphate adjuvants, for example, monophosphoryl lipid A (MPL), 3-O-deacylated MPL (3dMPL) e.g. GB-2220221, EP-A-0689454, optionally in the substantial absence of alum when used with pneumococcal saccharides e.g. WO00/56358; as well as aminoalkyl glucosamine phosphate compounds such as those described in U.S. Pat. No. 6,355,257; (7) combinations of 3dMPL with, for example, QS21 and/or oil-in-water emulsions, e.g., EP-A-0835318, EP-A-0735898, EP-A-0761231; (8) oligonucleotides comprising CpG motifs (Roman et al., *Nat. Med.*, 1997, 3, 849-854; Weiner et al., *PNAS USA*, 1997, 94, 10833-10837; Davis et al., *J. Immunol.* 1988, 160, 870-876; Chu et al., *J. Exp. Med.*, 1997, 186, 1623-1631; Lipford et al., *Eur. J. Immunol.* 1997, 27, 2340-2344; Moldoveanu et al., *Vaccine*, 1988, 16, 1216-1224, Krieg et al., *Nature*, 1995, 374, 546-549; Klinman et al., *PNAS USA*, 1996, 93, 2879-2883: Ballas et al., *J. Immunol.*, 1996, 157, 1840-1845; Cowdery et al., *J. Immunol.*, 1996, 156, 4570-4575; Halpern et al., *Cell. Immunol.*, 1996, 167, 72-78; Yamamoto et al., *Jpn. J. Cancer Res.*, 1988, 79, 866-873; Stacey et al., *J. Immunol*, 1996, 157, 2116-2122; Messina et al., *J. Immunol.*, 1991, 147, 1759-1764; Yi et al., *J. Immunol.*, 1996, 157, 4918-4925; Yi et al., *J. Immunol.*, 1996, 157, 5394-5402; Yi et al., *J. Immunol.*, 1998, 160, 4755-4761; and Yi et al., *J. Immunol.*, 1998, 160, 5898-5906; International patent applications WO96/02555, WO98/16247, WO98/18810, WO98/40100, WO98/55495, WO98/37919 and WO98/52581) i.e. containing at least one CG dinucleotide (a cytosine nucleotide followed by a guanosine nucleotide), with 5 methylcytosine optionally being used in place of cytosine; (9) a polyoxyethylene ether or a polyoxyethylene ester e.g. WO99/52549; (10) a polyoxyethylene sorbitan ester surfactant in combination with an octoxynol (WO01/21207) or a polyoxyethylene alkyl ether or ester surfactant in combination with at least one additional non-ionic surfactant such as an octoxynol (WO01/21152); (11) a saponin and an immunostimulatory oligonucleotide (e.g., a CpG oligonucleotide) (WO00/62800); (12) an immunostimulant and a particle of metal salt e.g. WO00/23105; (13) a saponin and an oil-in-water emulsion e.g. WO99/11241; (14) a saponin (e.g. QS21)+3dMPL+IL-12 (optionally+a sterol) e.g. WO98/57659; (15) detoxified mutants of a bacterial ADP-ribosylating toxin such as a cholera toxin (CT), a pertussis toxin (PT), or an *E. coli* heat-labile toxin (LT), particularly LT-K63 (where lysine is substituted for the wild-type amino acid at position 63) LT-R72 (where arginine is substituted for the wild-type amino acid at position 72), CT-S109 (where serine is substituted for the wild-type amino acid at position 109), and PT-K9/G129 (where lysine is substituted for the wild-type amino acid at position 9 and glycine substituted at position 129) (see, e.g., International Publication Nos. WO93/13202 and WO92/19265); (16) aminoalkyl glucosaminide 4-phosphates (AGP's), see, e.g., Johnson, D. A. et al.; Bioorg. Med. Chem. Lett., 1999 Aug. 2; 9(15):2273-8, (17) imidazoquinolines such as imiquimod (R-837) and resiquimod (R-848), see, e.g., Vasilakos, J. P. et al.; Cell. Immunol. 2000 Aug. 25; 204(1):64-74, (18) lipopolysaccharide mimetics (including monophosphoryl lipid A mimetics), such as non-saccharide phospholipids (e.g., simplified lipid A analogs lacking a disaccharide) described in Hawkins, L. D. et al; J. Pharmacol. Exp. Ther., 2002 February; 300(2):655-61 and U.S. Pat. No. 6,290,973; (19) adjuvants comprising natural or synthetic double-stranded RNA ("dsRNA"), which is generally made up of intermittent riboguanylic acid-ribocytidylic acid ([rG-rC]) and riboadenylic acid-polribouridylic acid ([rA-rU]) base pairs; for further information see, e.g., commonly owned PCT/US02/30423; and (20) other substances that act as immunostimulating agents to enhance the effectiveness of the composition.

Muramyl peptides include, but are not limited to, N-acetyl-muramyl-L-threonyl-D-isoglutamine (thr-MDP), N-acetyl-normuramyl-L-alanyl-D-isogluatme (nor-MDP), N-acetyl-muramyl-L-alanyl-D-isogluatminyl-L-alanine-2-(1'-2'-dipalmitoyl-sn-glycero-3-huydroxyphosphoryloxy)-ethylamine (MTP-PE), etc.

For additional examples of adjuvants, see *Vaccine Design, The Subunit and the Adjuvant Approach*, Powell, M. F. and Newman, M. J, eds., Plenum Press, 1995).

4. Formulation and Administration

The compositions of the present invention will generally include one or more pharmaceutically acceptable excipients. For example, vehicles such as water, saline, glycerol, polyethylene glycol, hyaluronic acid, ethanol, etc. may be used. Other excipients, such as wetting or emulsifying agents, biological buffering substances, and the like, may be present. A biological buffer can be virtually any solution which is pharmacologically acceptable and which provides the formulation with the desired pH, i.e., a pH in the physiological range. Examples include saline, various buffers including phosphate buffers, citrate buffers, borate buffers, succinate buffers, and histidine buffers, as well as saline buffer combinations, including phosphate buffered saline, Tris buffered saline, Hank's buffered saline, and the like.

Depending on the final dosage form, other excipients known in the art can also be introduced, including binders, disintegrants, fillers (diluents), lubricants, glidants (flow enhancers), compression aids, colors, sweeteners, preservatives, suspending/dispersing agents, film formers/coatings, flavors and printing inks.

Once formulated, the compositions of the invention can be administered parenterally, e.g., by injection (which may be needleless). The compositions can be injected subcutaneously, intraperitoneally, intravenously, intraarterially, intradermally, or intramuscularly, for example. Other modes of administration include nasal, mucosal, intraocular, rectal, vaginal, oral and pulmonary administration, suppositories, and transdermal or transcutaneous applications.

In some embodiments, the compositions of the present invention can be used for site-specific targeted delivery. For example, intravenous administration of the compositions can be used for targeting the lung, liver, spleen, blood circulation, or bone marrow.

Treatment may be conducted according to a single dose schedule or a multiple dose schedule. A multiple dose schedule is one in which a primary course of administration may be given, followed by one or more additional doses given at subsequent time intervals, chosen to maintain and/or reinforce the therapeutic response. The dosage regimen will also be, at least in part, determined by the need of the subject and be dependent on the judgment of the practitioner.

As previously indicated, the present invention relates to immunogenic pharmaceutical compositions, which comprise biodegradable polymer microparticles having adsorbed thereto toxoid and/or polysaccharide-containing antigens. As also indicated, the compositions are applicable to a wide range of vaccines, including vaccines directed to a wide array of pathogens or tumors.

Therefore, beneficial compositions include those containing the following antigens, either separately or in various combinations: tetanus antigen (e.g., tetanus toxoid antigen), diphtheria antigen (e.g., diphtheria toxoid antigen), hepatitis antigens (including HAV, HBV, HCV, HDV, HEV and HGV antigens), varicella virus (chickenpox) antigens, measles antigens, mumps antigens, rubella antigens, influenza antigens, meningococcal antigens (including meningitis A, meningitis B, meningitis C, meningitis W and meningitis Y antigens), diphtheria antigens, pertussis antigens, tetanus antigens, Hib antigens, and pneumococcal antigens.

Numerous such antigens are presently available, for example: (A) Recombinant DNA hepatitis B antigens (HbsAg) are available, which are made by inserting a portion of the HBV genome into yeast. (B) varicella zoster virus antigens are available, commonly prepared from lyophilized, live, attenuated varicella virus, designated the Oka strain. (C) Polio virus antigens are available, corresponding to either inactivated or live poliovirus, with inactivated poliovirus (IPV) antigens typically being preferred. IPV antigens are typically formalin-inactivated products, which are produced on cells, e.g., Vero cells or human diploid cells, and commonly correspond to three types of wild poliovirus. (D) Live measles virus antigens are frequently prepared from Edmonston B strains that have been further attenuated from the original strain (e.g., Moraten, Edmonston-Zagreb, Schwarz and Connaught strains). Measles antigens are commonly prepared in chick fibroblast cell cultures or in human fibroblasts. (E) Mumps virus antigens are typically live, attenuated virus antigens. They are frequently prepared from the Jeryl Lynn attenuated virus strain and are frequently grown in chick embryo cell culture. (F) Rubella virus antigens are also typically live, attenuated virus antigens. One presently known rubella virus antigen corresponds to live attenuated virus strain RA 27/3, and is prepared in human diploid cell culture. (G) Influenza antigen is frequently prepared from influenza viruses propagated in chicken embryos. The virus is inactivated, purified and treated with an organic solvent to remove surface glycoproteins. The antigens are commonly selected from two strains of influenza A and one strain of influenza B. The virus strains chosen for inclusion in influenza vaccine are typically reviewed annually to ensure that they include antigens that are expected to provide the best protection during the following winter. Influenza antigens also include live attenuated virus antigens and antigens derived from tissue culture. (H) Available meningococcal antigens include purified capsular polysaccharide antigens (Men-Ps) and protein-polysaccharide conjugate antigens (Men-conjugate), including antigens in which O-acetylated C-polysaccharide is conjugated to the protein CRM197 (Cross Reacting Material 197), and antigens in which de-O-acetylated C-polysaccharide is conjugated to tetanus toxoids. (I) Available pertussis antigens include both whole cell and acellular pertussis antigens. Acellular antigens have been developed to reduce the frequency and severity of both local and systemic adverse reactions associated with whole-cell pertussis antigens. Acellular pertussis antigens include, for example, pertussis toxoid, filamentous hemagglutinin and pertactin. (J) Available Hib antigens include polysaccharide antigens and polysaccharide-protein conjugate antigens, which can have the advantage of producing greater immune responses in infants and young children relative to purified polysaccharide antigen. Available Hib conjugate antigens differ in a number of ways, including the protein and the polysaccharide size. Examples include HbOC, PRP-OMP, PRP-T and PRP-D antigens. (K) Pneumococcal antigens are typically available as polysaccharide antigens or as conjugate antigens. An available polysaccharide pneumococcal vaccine, contains capsular polysaccharide antigens from each of 23 types of pneumococci (i.e., 1, 2, 3, 4, 5, 6B, 7F, 8, 9N, 9V, 10A, 11A, 12F, 14, 15B, 17F, 18C, 19A, 19F, 20, 22F, 23F and 33F, Danish nomenclature). An available pneumococcal conjugate vaccine (PCV) contains purified polysaccharides of the capsular antigens of seven $S.$ $pneumoniae$ serotypes (serotypes 4, 9V, 14, 18C, 19F, 23F and 6B), individually conjugated to CRM197.

Examples of antigen combinations for use in the present invention include all possible combinations of the above, for example, all possible combinations of DT, DPT, Hib, Hep, PV, Men, Pnu, Var and MMR, some specific examples of which follow:

```
DT
DT-Hep
DT-Men
DT-Hep-Men

DPT
DPT-Hib
DPT-Hep
DPT-PV
DPT-Pnu
DPT-Men
DPT-MMR
DPT-Var

DPT-Hib-Hep
DPT-Hib-PV
DPT-Hib-Pnu
DPT-Hib-Var
DPT-Hib-MMR
DPT-Hep-PV
DPT-Hep-Pnu
DPT-Hep-Var
DPT-Hep-MMR
DPT-PV-Pnu
DPT-PV-Var
DPT-PV-MMR
DPT-Men-Hib
DPT-Men-Hep
DPT-Men-PV
DPT-Men-Pnu
DPT-Men-Var
DPT-Men-MMR
DPT-Var-MMR
DPT-Var-Pnu
DPT-MMR-Pnu

DPT-Hib-Hep-PV
DPT-Hib-Hep-Pnu
DPT-Hib-Hep-MMR
DPT-Hib-Hep-Var
DPT-Hib-PV-Pnu
DPT-Hep-PV-Pnu
DPT-Hib-PV-MMR
DPT-Hib-PV-Var
DPT-Men-Hib-Hep
```

```
       -continued
DPT-Men-Hib-PV
DPT-Men-Hib-Pnu
DPT-Men-Hib-MMR
DPT-Men-Hib-Var
DPT-Men-Hep-PV
DPT-Men-Hep-Pnu
DPT-Men-Hep-MMR
DPT-Men-Hep-Var
DPT-Men-PV-Pnu
DPT-Men-PV-MMR
DPT-Men-PV-Var
DPT-Hib-Var-Pnu
DPT-Hib-Var-MMR
DPT-Hep-Var-PV
DPT-Hep-Var-Pnu
DPT-Hep-Var-MMR
DPT-Men-Var-Pnu
DPT-Men-Var-MMR
DPT-PV-Var-Pnu
DPT-PV-Var-MMR
DPT-Pnu-Var-MMR
DPT-Hib-Pnu-MMR
DPT-Hep-PV-MMR
DPT-Hep-Pnu-MMR
DPT-Men-Pnu-MMR
DPT-PV-Pnu-MMR DPT-Hib-Hep-PV-Pnu
DPT-Hep-PV-Pnu-Men
DPT-Hib-PV-Pnu-Men
DPT-Hib-Hep-Pnu-Men
DPT-Hib-Hep-P V-Men DPT-Hib-Hep-PV-Pnu-Men DPT-Hib-Hep-PV-Pnu-Men-Var-MMR
``` where, DT=diphtheria toxoid antigen and tetanus toxoid antigen; DTP=diphtheria toxoid antigen, tetanus toxoid antigen, arid pertussis antigen (including whole-cell and acellular pertussis antigens, typically acellular); Hib=*Haemophilus influenzae* type b antigen (including polysaccharide and conjugate antigens); Hep=hepatitis antigen (including HAV antigen, HBV antigen, HCV antigen, HDV antigen, HEV antigen, HGV antigen, and combinations thereof, e.g., HAV antigen-HBV antigen); PV=polio antigen (including inactivated or live antigens, e.g., inactivated antigens from three polio strains); Men=meningococcal (*Neisseria meningitidis*) antigen (including conjugate and polysaccharide antigens, typically conjugate antigens, and including antigens from Men A, B, C, W, Y and combinations, e.g., Men A,C antigens, Men A,B,C antigens, Men A,C,W,Y antigens, and Men A,B,C, W,Y antigens); Pnu=pneumococcal (*Streptococcus pneumoniae*) antigen (including conjugate and polysaccharide antigens, typically conjugate antigens); Var=Varicella zoster virus antigen (for example, live, attenuated varicella virus); MMR=measles, mumps and rubella antigens (for example, live, attenuated measles, mumps and rubella virus antigens).

Recommended administration schedules for vaccines containing several of the above antigens are available. As a specific example, the U.S. Department of Health and Human Services, Centers for Disease Control and Prevention, National Immunization Program, has published its recommended childhood and adolescent immunization schedules. The present schedules for the United States 2003 are illustrated, in part, in FIG. 1 and is summarized below:

The schedules to follow are based on Recommended Childhood and Adolescent Immunization Schedule—United States 2003, from the U.S. Department of Health and Human Services, Centers for Disease Control and Prevention, National Immunization Program.

Hepatitis B. (A) First Dose. Birth to two months. Children whose mothers are hepatitis B surface antigen positive or whose hepatitis B surface antigen status is unknown are recommended to get this dose within 12 hours of birth. All infants are recommended to receive the first dose of hepatitis B vaccine soon after birth and before hospital discharge; the first dose may also be given by age 2 months if the infant's mother is hepatitis B surface antigen negative. Only monovalent hepatitis B vaccine is presently recommended for the birth dose. Monovalent or combination vaccine containing Hep B may be used to complete the series; four doses of vaccine may be administered if combination vaccine is used. Infants born to hepatitis B surface antigen positive mothers are recommended to receive hepatitis B vaccine and 0.5 milliliters of hepatitis B immune globulin (H BIG) within 12 hours of birth at separate sites. Infants born to mothers whose hepatitis B surface antigen status is unknown are recommended to receive the first dose of the hepatitis B vaccine series within 12 hours of birth. Maternal blood is recommended to be drawn at the time of delivery to determine the mother's hepatitis B surface antigen status; if the test is positive, the infant is recommended to receive H BIG as soon as possible (and no later than one week). (B) Second Dose. One to four months, but at least 4 weeks after the first dose. The second dose is recommended to be given at least 4 weeks after the first dose. Hib-containing vaccine is not recommended to be administered before age 6 weeks. For infants born to hepatitis B surface antigen positive mothers, the second dose is recommended at age 1-2 months and the vaccination series is recommended to be completed (third or fourth dose) at age 6 months. (c) Third Dose: six to 18 months, but at least 16 weeks after the first dose and at least 8 weeks after the second dose. In general, it is recommended that the last dose in the vaccination series (third or fourth dose) is not to be administered before age 6 months. However, for infants born to hepatitis B surface antigen positive mothers, the vaccination series is recommended to be completed (third or fourth dose) at age 6 months. (D) Catch-up schedule for children age 4 months through 6 years. All children and adolescents who have not been immunized against hepatitis B are recommended to begin the Hep B vaccination series during any visit. Providers are recommended to make special efforts to immunize children who were born in, or whose parents were born in, areas of the world where hepatitis B virus infection is moderately or highly endemic. Minimum Interval Between Dose One to Dose Two: 4 weeks. Minimum Interval Between Dose Two to Dose Three: 8 weeks (and 16 weeks after first dose). (E) Catch-up schedule for children age 7 through 18 years. Minimum Interval Between Dose One to Dose Two: 4 weeks. Minimum Interval Between Dose Two to Dose Three: 8 weeks (and 16 weeks after first dose).

Diphtheria, Tetanus, Pertussis (DTaP). (A) First Dose: Two months. (B) Second Dose: Four months. (C) Third Dose: Six months. (D) Fourth Dose: 15 to 18 months. The fourth dose of DTaP may be administered as early as age 12 months, provided 6 months have elapsed since the third dose, and the child is unlikely to return at age 15 to 18 months. (E) Fifth Dose: 4 to 6 years. (F) Catch-up schedule for children age 4 months through 6 years. Minimum Interval Between Dose One to Dose Two: 4 weeks. Minimum Interval Between Dose Two to Dose Three: 4 weeks. Minimum Interval Between Dose Three to Dose Four: 6 months. Minimum Interval Between Dose Four to Dose Five: 6 months. The fifth dose is not necessary if the fourth dose was given after the 4th birthday.

Tetanus and Diphtheria. (A) Recommended at age 11 to 12 years if at least 5 years have elapsed since the last dose of tetanus and diphtheria toxoid-containing vaccine. Subsequent routine Td boosters are recommended every 10 years.

(B) Catch-up schedule for children age 7 through 18 years. Minimum Interval Between Dose One to Dose Two: 4 weeks. Minimum Interval Between Dose Two to Dose Three: 6 months. Minimum Interval Between Dose Three to Booster Dose: 6 months, if 1st dose given at age less than 12 months and if current age less then 11 years; 5 years, if 1 st dose given at age 12 months or older and if 3rd dose given at less than 7 years of age and current age 11 or older; 10 years, if 3rd dose given at age 7 years or older. (Note: for children age 7 to 10 years, the interval between the third and booster dose is determined by the age when the first dose was given. For adolescents age 11 to 18 years, the interval is determined by the age when the third dose was given.)

*Haemophilus influenzae* Type b. (A) First Dose: Two months. (B) Second Dose: Four months. (C) Third Dose: Six months. If PRP-OMP is administered at ages 2 and 4 months, a dose at age 6 months is not required. (D) Fourth Dose: 12 to 15 months. (E) Catch-up schedule for children age 4 months through 6 years. (Note: Vaccine is not generally recommended for children age 5 years or older.) Dose one to Dose two minimum intervals: 4 weeks, if first dose given at age less than 12 months; 8 weeks (as a final dose), if first dose given at age 12 to 14 months; if first dose given at age 15 months or older, then no further doses are recommended. Dose two to Dose three minimum intervals: 4 weeks, if current age less than 12 months; 8 weeks (as final dose), if second dose given at age less than 15 months and if current age is 12 months or older; if second dose given at age 15 months or older, no further doses needed. (If current age is less than 12 months and the first 2 doses were PRP-OMP, the third and final doses are recommended to be given at age 12 to 15 months and at least 8 weeks after the second dose.) Dose three to Dose four minimum intervals: 8 weeks (as final dose). This dose is only recommended for children age 12 months to 5 years who received 3 doses before age 12 months.

Inactivated Polio. (A) First Dose: Two months. (B) Second Dose: Four months. (C) Third Dose: 6 to 18 months. (D) Fourth Dose: 4 to 6 years. E) Minimum Interval Between Dose One to Dose Two: 4 weeks. Minimum Interval Between Dose Two to Dose Three: 4 weeks. Minimum Interval Between Dose Three to Dose Four: 4 weeks. For children who received an all IPV or all OPV series, a fourth dose is not necessary if third dose was given at age 4 years or greater. If both OPV and IPV were given as part of a series, a total of four doses are recommended to be given, regardless of the child's current age. (D) Catch-up schedule for children age 7 through 18 years. (Note: this vaccine is not generally recommended for persons age 18 years or older.) Minimum Interval Between Dose One to Dose Two: 4 weeks. Minimum Interval Between Dose Two to Dose Three: 4 weeks.

Measles, Mumps, Rubella. (A) First Dose: 12 to 15 months. (B) Second Dose: 4 to 6 years. The second dose of MMR is recommended routinely at age 4 to 6 years but may be administered during any visit, provided at least 4 weeks have elapsed since the first dose and that both doses are administered beginning at or after age 12 months. Those who have not previously received the second dose are recommended to complete the schedule by the 11 to 12 year old visit. (C) Catch-up schedule for children age 4 months through 6 years. Minimum age: 12 months. Minimum Interval Between Dose One to Dose Two: 4 weeks. The second dose of MMR is recommended routinely at age 4 to 6 years, but may be given earlier if desired. (D) Catch-up schedule for children age 7 through 18 years. Minimum Interval Between Dose One to Dose Two: 4 weeks.

Varicella. 12 to 18 months. Varicella vaccine is recommended at any visit at or after age 12 months for susceptible children (i.e., those who lack a reliable history of chickenpox). Susceptible persons 13 years of age or older are recommended to receive 2 doses, given at least 4 weeks apart. Catch-up schedule for children age 7 through 18 years. Minimum Interval Between Dose One to Dose Two: 4 weeks.

Pneumococcal Conjugate Vaccine. The heptavalent pneumococcal conjugate vaccine (PCV) is recommended for all children aged 2 to 23 months and for certain children aged 24 to 59 months. (A) First Dose: Two months. (B) Second Dose: Four months. (C) Third Dose: Six months. (D) Fourth Dose: 12 to 15 months. (E) Catch-up schedule for children age 4 months through 6 years. (Note: this vaccine is not generally recommended for children age 5 years or older.) Dose one to Dose two minimum intervals: if first dose given at age less than 12 months and if current age less than 24 months, then 4 weeks; if first dose given at age 12 months or older or if current age 24 to 59 months, then 8 weeks (as final dose); if first dose given at age 24 months or older, then for healthy children, no further doses needed. Dose two to Dose three minimum intervals: if second dose given at age less than 12 months, then 4 weeks; if second dose given at age 12 months or older, then 8 weeks (as final dose); if second dose given at age 24 months or older, then for healthy children, no further doses needed. Dose three to Dose four minimum intervals: 8 weeks (as final dose). This dose only necessary for children age 12 months to 5 years who received 3 doses before age 12 months.

Pneumococcal polysaccharide vaccine (PPV). Recommended in addition to PCV for certain high-risk groups.

Hepatitis A. The hepatitis A series may be given to children two years of age or older. Hepatitis A vaccine is recommended for use in selected states and regions, and for certain high-risk groups.

Influenza. Influenza vaccine is recommended annually for children 6 months of age or older with certain risk factors (including but not limited to asthma, cardiac disease, sickle cell disease, HIV and diabetes), and can be administered to all others wishing to obtain immunity. Children 12 years of age or younger are recommended to receive vaccine in a dosage appropriate for their age. Children 8 years of age or younger who are receiving influenza vaccine for the first time are recommended to receive two doses separated by at least 4 weeks.

These schedules pertain to children through age 18 years. Any dose not given at the recommended age is, in general, recommended to be given at a subsequent time, when indicated and feasible. Obviously, additional schedules can be established for the various vaccines listed.

In certain embodiments, the administration times for a vaccine in accordance with the present invention will be based upon the recommended schedule illustrated in FIG. 1 or described above. For example, a time for administration of a vaccine in accordance with the present invention can be selected based upon the recommended schedule for a vaccine that contains one (or more) antigens found within the vaccine of the present invention.

As a specific example, vaccine compositions in accordance with the present invention that contain diphtheria, pertussis and tetanus antigens (and optionally one or more additional antigens) can be administered at any of the following times: two months, four months, six months, 15 to 18 months and 4 to 6 years, among other times. As another specific example, a vaccine containing DTP/HepB/Hib/PV/Pnu (or any combination of these) can be administered at 2 months, 4 months, 6 months, or 15 months, among others. As another specific example, a vaccine containing DTP/HepB/PV (or any combination of these) can be administered at 4-6 years, among others. As another specific example, a vaccine containing DTP/HepB/Hib/PV/Pnu/MMR/Var (or any combination of these) can be administered at 15 months, among others. As another specific example, vaccine compositions that contain diphtheria and tetanus antigens (and optionally one or more additional antigens) can be administered at 11-18 years (and up), among others. As another specific example, a vaccine containing DT/HepB can be administered at 11-18 years (and up), among others. As yet another specific example, a vaccine containing DT/HepB/MMR Var (or any combination of these) can be administered at 11-18 years (and up) among others. And so forth.

C. Experimental

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

EXAMPLE 1

Efficiency of Adsorption of Tetanus Toxoid and Diphtheria Toxoid to PLG particles Microparticles are prepared using a 6% w/v solution of RG503 polymer (a PLG Polymer having a 50:50 lactide/glycolide molar ratio and a molecular weight of approximately 34 kDaltons, available from Boehringer Ingelheim) in methylene chloride. 10 ml of this solution is homogenized with 2.5 ml PBS using a 10-mm probe of a homogenizer (Ultra-Turrax T25 IKA-Labortechnik, Germany) for three minutes at 23,000 rpm, thereby forming a water-in-oil emulsion. This emulsion is then added to 50 ml of distilled water containing 6 μg/ml dioctyl sodium sulfosuccinate (DSS) (available from Sigma, USA) and homogenized at very high speed using a homogenizer with a 20-mm probe (ES-15 Omni International, GA, USA) for 25 minutes in an ice bath. This resulted in a water-in-oil-in-water emulsion, which is stirred at 1000 rpm for 12 h at room temperature, allowing the methylene chloride to evaporate. The resulting microparticles contain 0.05% DSS wt/wt. The size distribution of the resulting microparticle suspension is determined using a particle size analyzer (Master Sizer, Malvern Instruments, UK), and is found to be between 0.8 and 1.2 μm.

Tetanus and Diphtheria toxoids, TT and DT, are adsorbed to the 0.05% DSS PLG particles in various buffers with different pH values. The adsorption is carried out by incubating 100 mg of the above microparticle suspension with 1 mg or 0.5 mg of DT or TT, respectively, in 10 mM of buffer overnight, while rocking at 4° C. The buffers are as follows: PBS pH 7, phosphate pH 7, Citrate pH 5, Borate pH9, Succinate pH5.5, Succinate pH 5, and Histidine pH 5.

The suspension is centrifuged the next day, and the supernatant evaluated for concentration of unbound protein by HPLC (to establish % adsorption efficiency by depletion). Protein on particles is evaluated by first washing the particles with water to remove the unbound protein, followed by lyophilization. The amount of adsorbed protein is determined by hydrolyzing 10 mg of lyophilized particles with 2 ml 0.2N NaOH and 5% SDS for 4 hours followed by a BCA proteins assay (to establish % adsorption efficiency on particles). The results are presented in Tables 1A and 1B below.

TABLE 1A

| Buffer | % Target Load wt/wt | % Adsorption efficiency TT by depletion | % Adsorption efficiency TT on particles |
|---|---|---|---|
| PBS pH 7 | 1% | 0 | 0 |
| Phosphate pH 7 | 1% | 10 | 0 |
| Citrate pH 5 | 1% | 93 | 81 |
| Borate pH 9 | 1% | 0 | 0 |
| Succinate pH 5.5 | 1% | 60 | 68 |
| Succinate pH 5 | 1% | 89 | ND |
| Succinate pH 5 | 0.5 | 88 | ND |
| Histidine pH 5 | 0.5 | ND | 60 |

TABLE 1B

| Buffer | % Target Load wt/wt | % Adsorption efficiency DT by depletion | % Adsorption efficiency DT on particles |
|---|---|---|---|
| PBS pH 7 | 1% | 0 | 0 |
| Phosphate pH 7 | 1% | 0 | 0 |
| Citrate pH 5 | 1% | 70 | 68 |
| Borate pH 9 | 1% | ND | ND |
| Succinate pH 5.5 | 1% | 17 | 0 |
| Succinate pH 5 | 1% | 35 | ND |
| Succinate pH 5 | 0.5 | 32 | ND |
| Histidine pH 5 | 0.5 | ND | 52 |

EXAMPLE 2

Adsorption and Release of Tetanus Toxoid and Diphtheria Toxoid to/from PLG Particles Microparticles are prepared as described in Example 1. DT and TT proteins are adsorbed to microparticles at a target load of 0.25%, 0.5% or 1% by incubating 100 mg of the above microparticle suspension with an appropriate amount of DT or TT in 10 mM of Histidine buffer overnight, while rocking at 4° C. The suspension is centrifuged the next day, and the supernatant evaluated for concentration of unbound protein by HPLC to establish % adsorption efficiency by depletion. The results are presented in column 2 of Table 2 below and in FIG. 2.

The amount of protein released from microparticles was determined by incubating 10 mg of lyophilized, unwashed particles with 1 ml water and left rocking at 4° C. for one hour, centrifuged, and the supernatant analyzed for released protein by HPLC as above. The results are presented in column 3 of Tables 2A and 2B below and in FIG. 2.

TABLE 2A

| Formulation | % adsorbed by depletion | % released in 1hour |
|---|---|---|
| 0.25% DT | 74.1 | 9.7 |
| 0.50% DT | 68.5 | 16.1 |
| 1.00% DT | 67.6 | 19.8 |

TABLE 2B

| Formulation | % adsorbed by depletion | % released in 1 hour |
|---|---|---|
| 0.25% TT | >96.7 | <1.6 |
| 0.50% TT | >97 | <1.6 |
| 1.00% TT | 98.6 | 1.2 |

EXAMPLE 3

Adsorption and Release of Meningococcal Protein-Polysaccharide Conjugates to/from PLG Particles (RG503/0.05% DSS)

Microparticles containing 0.05% DSS wt/wt are prepared as in Example 1 above. Protein-polysaccharide conjugate meningococcal antigens in which purified capsular polysaccharide antigens from either Men-A, Men-B, Men-C or Men-W are adsorbed to the microparticles.

Meningococcal conjugate antigens are adsorbed to microparticles at a target load of 1% by incubating 100 mg of the microparticles with 1 mg of meningococcal conjugate antigen in 10 mM of Histidine buffer overnight, while rocking at 4° C. The suspension is centrifuged the next day, and the supernatant evaluated for concentration of unbound conjugate antigen by HPLC to establish % adsorption efficiency by depletion. The results are presented in column 2 of Table 3 below.

Figure 3:
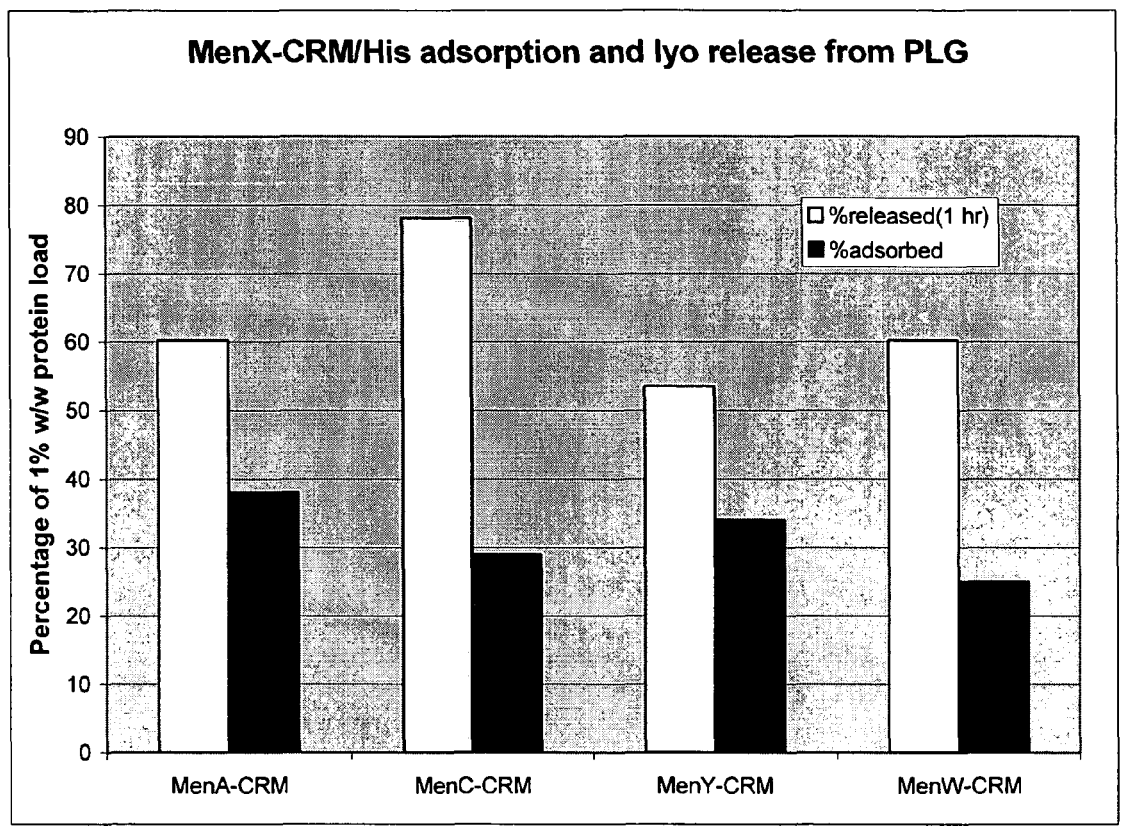
FIG. 3 is a bar graph illustrating % adsorption and % release for Men-X Crm conjugate from PLG particles.

Conjugate antigen adsorbed to particles is evaluated by first washing the particles with water to remove the unbound conjugate antigen, followed by lyophilization. The amount of adsorbed conjugate antigen is determined by hydrolysis of the lyophilized particles, followed by a BCA proteins assay as above. The results are presented in column 3 of Table 3 and in FIG. 3.

To determine the amount of protein released from particles, an aliquot of the particle-antigen suspension is lyophilized without washing, and 10 mg of the lyophilized particles are then incubated with 1 ml water and left rocking at 4° C. for one hour. The results are presented in column 4 of Table 3 below and in FIG. 3.

TABLE 3

| formulation | % adsorbed by depletion | % adsorbed by hydrolysis | % 1 hour release |
|---|---|---|---|
| MenA-CRM | 38 | 31 | 60.2 |
| MenC-CRM | 29 | 25 | 78.1 |
| MenY-CRM | 34 | 40 | 53.5 |
| MenW-CRM | 25 | 29 | 60.2 |

EXAMPLE 4

Immunogenicity of Tetanus Toxoid (TT) and Diphtheria Toxoid (DT) Formulated with PLG Particles Mouse Study.

For the study, a PLG/DSS microparticle suspension is prepared as described in Example 1. Tetanus and Diphtheria toxoids, DT and TT, are adsorbed to the microparticles at a target load of 0.5% or 1% by incubating 100 mg of the above microparticle suspension with an appropriate amount of DT or TT in 10 mM of Histidine buffer overnight, while rocking at 4° C. Then, each formulation was tested singly (PLG/TT or PLG/DTT) or in combination (PLG/DT+PLG/TT). The equivalent Alum formulations (Alum/TT or Alum/DTT, and (Alum/DTT+Alum/TT)) were also included in the study for comparison. Mice were injected at the tibialis anterior with 50 µl per leg on day 0 and day 14. Sera were collected on day 28 by orbital sinus bleed.

ELISA Assay.

The presence of IgG antibody was determined for each mouse by testing eight serial dilutions of serum starting at 1/50 on plates that were coated with DT-CRM or TT antigen. A positive control and positive mouse serum reference were tested on each plate for a system-suitable control. The presence of serum antibodies was detected with a second antibody conjugated to Horseradish Peroxidase in combination with a colorimetric substrate, which adsorbs at 450 nm. The titers were defined as the reciprocal serum dilution that gave an optical density of 0.5 ELISA absorbency. Titers were obtained by interpolation from a four-parameter curve fit of absorbance versus dilution. The geometric mean titers (GMT) were calculated and the mice having a titer ≥ of 50 were reported as responders. The results are presented in Tables 4A-C below. As can be seen from these results: (1) No difference was found in titers elicited with PLG microparticle prepared at 0.5% or 1% target load for both antigens TT and DT. (2) The combination of both antigens formulated with PLG or Alum enhanced the responses to TT by ~2-fold. (3) Overall, based on these results, the responses elicited with PLG/TT and PLG/DT are comparable to Alum/TT and Alum/DT.

TABLE 4A

2wp2 DT antibody Titers

| | GMT #Responders | LCL | UCL |
|---|---|---|---|
| PLG/DT (0.5%) | 17,277 | 11,718 | 25,473 |
| PLG/DT (1.0%) | 23,938 | 13,184 | 43,464 |
| PLG/DT + PLG/TT | 17,786 | 9,389 | 33,695 |
| Alum/DT | 54,166 | 40,022 | 73,308 |
| Alum/DT + Alum/TT | 39,635 | 24,696 | 63,609 |

LCL/UCL = 95% Confidence Limits = Mean ± (t × SEM)
All calculations were performed using log transformed titer values; final geometric mean titers and 95% Confidence Limits shown were obtained by taking the antilog.

TABLE 4B

2wp2 TT antibody Titers

| | GMT #Responders | LCL | UCL |
|---|---|---|---|
| PLG/TT (0.5%) | 32,182 | 20,408 | 50,750 |
| PLG/TT (1.0%) | 41,431 | 34,842 | 49,265 |
| PLG/DT + PLG/TT | 61,992 | 36,882 | 104,199 |
| Alum/TT | 36,860 | 26,672 | 50,939 |
| Alum/DT + Alum/TT | 70,825 | 55,538 | 90,322 |

LCL/UCL = 95% Confidence Limits = Mean ± (t × SEM)
All calculations were performed using log transformed titer values; final geometric mean titers and 95% Confidence Limits shown were obtained by taking the antilog.

EXAMPLE 5

Immunogenicity of Meningococcal Protein-Polysaccharide Conjugates Formulated with PLG Particles (RG503/0.05% DSS) and Alum Microparticles containing 0.05% DSS wt/wt are prepared as in Example 1 above. Protein-polysaccharide conjugate meningococcal antigens in which purified capsular polysaccharide antigens from Men-C are conjugated to either $CRM_{197}$ diphtheria toxoid or to ADH, obtained from Chiron Vaccines, Siena, Italy, are adsorbed to the microparticles. Meningococcal conjugate antigens are adsorbed to the microparticles at a target load of 1.0% by incubating 100 mg of the microparticles with 1.0 mg of meningococcal conjugate antigen in PBS at pH 7.0 overnight, while rocking at 4° C. Mice were injected at the tibialis anterior with 50 μl per leg on day 0 and day 14. Sera were collected on day 28 by orbital sinus bleed.

The presence of IgG antibody was determined for each mouse by testing eight serial dilutions of serum starting at 1/50 on plates that were coated with Men-C ADH or Men-C CRM antigen. A positive control and positive mouse serum reference were tested on each plate for a system-suitable control. The presence of serum antibodies was detected with a second antibody conjugated to Horseradish Peroxidase in combination with a colorimetric substrate, which adsorbs at 450 nm. The titers were defined as the reciprocal serum dilution that gave an optical density of 0.5 ELISA absorbency. Titers were obtained by interpolation from a four-parameter curve fit of absorbance versus dilution. The geometric mean titers (GMT) were calculated for IgG total and $IgG_1$ (for Men-C CRM). The results are presented in Table 5 below. As can be seen from these results, antigen formulated with PLG compared favorably to antigen formulated with alum.

TABLE 5

| Formulation | MenC ADH (cut off: 0.5) IgG total | | | MenC CRM (cut off: 0.5) IgG total | | | MenC CRM (cut off: 0.5) IgG1 | | |
| --- | --- | --- | --- | --- | --- | --- | --- | --- | --- |
| | GMT | lower | upper | GMT | lower | upper | GMT | lower | upper |
| MenC CRM/PLG | 205 | 176 | 238 | 1,553 | 1,427 | 1,691 | 33,664 | 29,782 | 38,053 |
| MenC CRM/Alum | 82 | 59 | 114 | 1,381 | 1,244 | 1,533 | 33,017 | 30,372 | 35,892 |

Although preferred embodiments of the subject invention have been described in some detail, it is understood that obvious variations can be made without departing from the spirit and the scope of the invention.

The invention claimed is:

1. An immunogenic composition comprising: (a) polymer microparticles comprising a biodegradable polymer selected from a poly(α-hydroxy acid), a polyhydroxy butyric acid, a polycaprolactone, a polyorthoester, a polyanhydride, a polycyanoacrylate, and combinations thereof and an anionic surfactant; (b) a polysaccharide-containing antigen, a diphtheria toxoid antigen and a tetanus toxoid antigen adsorbed to the polymer microparticles; and (c) a pharmaceutically acceptable excipient.

2. The immunogenic composition of claim 1, further comprising an additional antigen.

3. The immunogenic composition of claim 2, wherein the additional antigen is adsorbed to the surface of the microparticles.

4. The immunogenic composition of claim 2, wherein the additional antigen is a polypeptide-containing antigen.

5. The immunogenic composition of claim 2, wherein the additional antigen is an additional polysaccharide-containing antigen.

6. The immunogenic composition of claim 2, wherein the additional antigen is an additional conjugate antigen comprising polysaccharide and polypeptide regions.

7. The immunogenic composition of claim 2, wherein the additional antigen is a polynucleotide-containing antigen.

8. The immunogenic composition of claim 2, wherein the additional antigen is derived from a tumor cell.

9. The immunogenic composition of claim 2, wherein the additional antigen is derived from a pathogenic organism.

10. The immunogenic composition of claim 9, wherein the pathogenic organism is selected from a virus, a bacterium, a fungus and a parasite.

11. The immunogenic composition of claim 9, wherein the pathogenic organism is selected from hepatitis virus, varicella, poliovirus, measles, mumps, rubella, influenza virus, *Neisseria meningitides*, pertussis, *Haemophilus influenzae* type b, HIV and *Streptococcus pneumoniae*.

12. The immunogenic composition of claim 9, wherein the pathogenic organism is pertussis.

13. The immunogenic composition of claim 12, wherein the composition comprises a *hepatitis*virus antigen.

14. The immunogenic composition of claim 13, wherein the composition comprises an antigen selected from a *Haemophilus influenzae* type b antigen, a poliovirus antigen, a *Neisseria meningitidis* antigen, and a *Streptococcus pneumoniae* antigen.

15. The immunogenic composition of claim 12, wherein the composition comprises a *Haemophilus influenzae* type b antigen.

16. The immunogenic composition of claim 15, wherein the composition comprises an antigen selected from a hepatitis virus antigen, a poliovirus antigen, a *Neisseria meningitides* antigen and a *Streptococcus pneumoniae* antigen.

17. The immunogenic composition of claim 12, wherein the composition comprises a poliovirus antigen.

18. The immunogenic composition of claim 17, wherein the composition comprises an antigen selected from a hepatitis virus antigen, a *Haemophilus influenzae* type b antigen, a *Neisseria meningitidis* antigen and a *Streptococcus pneumoniae* antigen.

19. The immunogenic composition of claim 12, wherein the composition comprises a *Neisseria meningitidis* antigen.

20. The immunogenic composition of claim 19, wherein the composition comprises an antigen selected from a hepatitis virus antigen, a *Haemophilus influenzae* type b antigen, poliovirus antigen, and a *Streptococcus pneumoniae* antigen.

21. The immunogenic composition of claim 12, wherein the composition comprises a *Streptococcus pneumoniae* antigen.

22. The immunogenic composition of claim 21, wherein the composition comprises an antigen selected from a hepatitis virus antigen, a *Haemophilus influenzae* type b antigen, poliovirus antigen and a *Neisseria meningitidis* antigen.

23. The immunogenic composition of claim 9, wherein the additional antigen is a killed or attenuated pathogenic organism.

24. The immunogenic composition of claim 1, wherein the biodegradable polymer is a poly(α-hydroxy acid).

25. The immunogenic composition of claim 1, further comprising a supplemental immunological adjuvant.

26. The immunogenic composition of claim 25, wherein the supplemental immunological adjuvant is adsorbed to the surface of the microparticles.

27. The immunogenic composition of claim 25, wherein the supplemental immunological adjuvant is entrapped within the microparticles.

28. The immunogenic composition of claim 25, wherein the supplemental immunological adjuvant is selected from CpG oligonucleotides, double-stranded RNA, *E. coli* heat-labile toxins, liposaccharide phosphate compounds, liposaccharide phosphate mimetics, and submicron emulsions that comprise squalene, a sorbitan ester and a polyoxyethylene sorbitan ester.

29. The immunogenic composition of claim 1, wherein the polysaccharide containing antigen adsorbed to the microparticles is selected from a Hib polysaccharide antigen, a Hib conjugate antigen, a meningococcal polysaccharide antigen, a meningococcal conjugate antigen, a pneumococcal polysaccharide antigen, and a pneumococcal conjugate antigen.

30. The immunogenic composition of claim 29, wherein the polysaccharide containing antigen is a meningococcal conjugate antigen.

31. The immunogenic composition of claim 30, wherein the meningococcal conjugate antigen is a meningitis C conjugate antigen.

32. The immunogenic composition of claim 1, wherein said polysaccharide-containing antigen is selected from a Hib polysaccharide antigen, a meningococcal polysaccharide antigen and a pneumococcal polysaccharide antigen.

33. The immunogenic composition of claim 1, wherein said polysaccharide-containing antigen is selected from a Hib conjugate antigen, a meningococcal conjugate antigen, and a pneumococcal conjugate antigen.

34. The immunogenic composition of claim 1, wherein said polysaccharide-containing antigen is a Hib conjugate antigen.

35. The immunogenic composition of claim 1, wherein said anionic surfactant is selected from sodium dodecyl sulfate, sodium lauryl sulfate and dioctyl sodium sulfosuccinate.

36. The immunogenic composition of claim 1, wherein said anionic surfactant is dioctyl sodium sulfosuccinate.

37. The immunogenic composition of claim 1, wherein said anionic surfactant is dioctyl sodium sulfosuccinate and wherein said biodegradable polymer is a poly(lactide-co-glycolide) having a lactide:glycolide molar ratio ranging from 40:60 to 60:40.

38. The immunogenic composition of claim 1, wherein said polysaccharide-containing antigen is adsorbed to said microparticles independently of said diphtheria and tetanus toxoid antigens.

39. The immunogenic composition of claim 31, wherein said polysaccharide-containing antigen is a meningococcal conjugate antigen that is adsorbed to said microparticles in the presence of a phosphate buffer.

40. The immunogenic composition of claim 1, wherein said composition comprises histidine.

41. The immunogenic composition of claim 30, wherein the meningococcal conjugate antigen comprises a diphtheria toxoid carrier protein.

42. The immunogenic composition of claim 30, wherein the meningococcal conjugate antigen comprises a $CRM_{197}$ carrier protein.

43. The immunogenic composition of claim 31, wherein the meningococcal conjugate antigen comprises a diphtheria toxoid carrier protein.

44. The immunogenic composition of claim 31, wherein the meningococcal conjugate antigen comprises a $CRM_{197}$ carrier protein.

* * * * *